United States Patent [19]
Okazaki et al.

[11] Patent Number: 5,945,501
[45] Date of Patent: Aug. 31, 1999

[54] EPOXY RESIN COMPOSITIONS INCLUDING NOVEL PHENOL NOVOLAK CONDENSATES PRODUCED FROM BIS (METHOXYMETHYL)BIPHENYLS

[75] Inventors: Katuhiko Okazaki; Mikito Kashima; Yumiki Noda; Hiroshi Jibiki; Takashi Honma, all of Ube, Japan

[73] Assignees: UBE Industries, Ltd.; Meiwa Plastic Industries, both of Ube, Japan

[21] Appl. No.: 08/759,680

[22] Filed: Dec. 6, 1996

Related U.S. Application Data

[62] Division of application No. 08/530,735, Sep. 19, 1995, Pat. No. 5,612,442.

[30] Foreign Application Priority Data

Sep. 20, 1994 [JP] Japan ..................................... 6-251328
Feb. 21, 1995 [JP] Japan ..................................... 7-32635

[51] Int. Cl.$^6$ .................................................. C08G 59/00
[52] U.S. Cl. ............................. 528/97; 528/87; 528/219; 525/523; 525/534; 549/517; 549/546
[58] Field of Search ............................... 528/87, 97, 219; 525/523, 534; 549/546, 517

[56] References Cited

U.S. PATENT DOCUMENTS

| | | | |
|---|---|---|---|
| 3,576,188 | 4/1971 | Tanis | 130/27 |
| 3,936,510 | 2/1976 | Harris et al. | 260/831 |
| 3,987,105 | 10/1976 | Yardley | 260/600 |
| 4,248,976 | 2/1981 | Clubley et al. | 524/151 |
| 4,992,597 | 2/1991 | Mina et al. | 568/720 |
| 5,488,182 | 1/1996 | Kobayashi et al. | 568/660 |

FOREIGN PATENT DOCUMENTS

| | | |
|---|---|---|
| 26 48 701 | 5/1977 | Germany . |
| 47-13782 | 4/1972 | Japan . |
| 47-15111 | 5/1972 | Japan . |
| 48-10960 | 4/1973 | Japan . |
| 1-95124 | 4/1989 | Japan . |
| 3-81321 | 4/1991 | Japan . |
| 4-110317 | 4/1992 | Japan . |
| 5-78457 | 3/1993 | Japan . |
| 5-117350 | 5/1993 | Japan . |
| 1221772 | 2/1971 | United Kingdom . |
| 1544417 | 4/1979 | United Kingdom . |

*Primary Examiner*—Randy Gulakowski
*Attorney, Agent, or Firm*—Finnegan, Henderson, Farabow, Garrett & Dunner L.L.P.

[57] ABSTRACT

A bis(methoxymethyl)biphenyl having the formula (I):

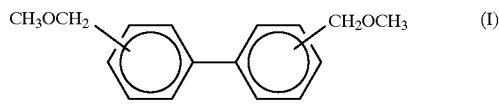

which is capable of producing by a dehalogenating coupling of a halogenated methoxymethylbenzene and which is useful as an intermediate for a phenol novolak condensate, an epoxy resin curing agent, an epoxy resin composition, or a phenol resin composition.

7 Claims, 12 Drawing Sheets

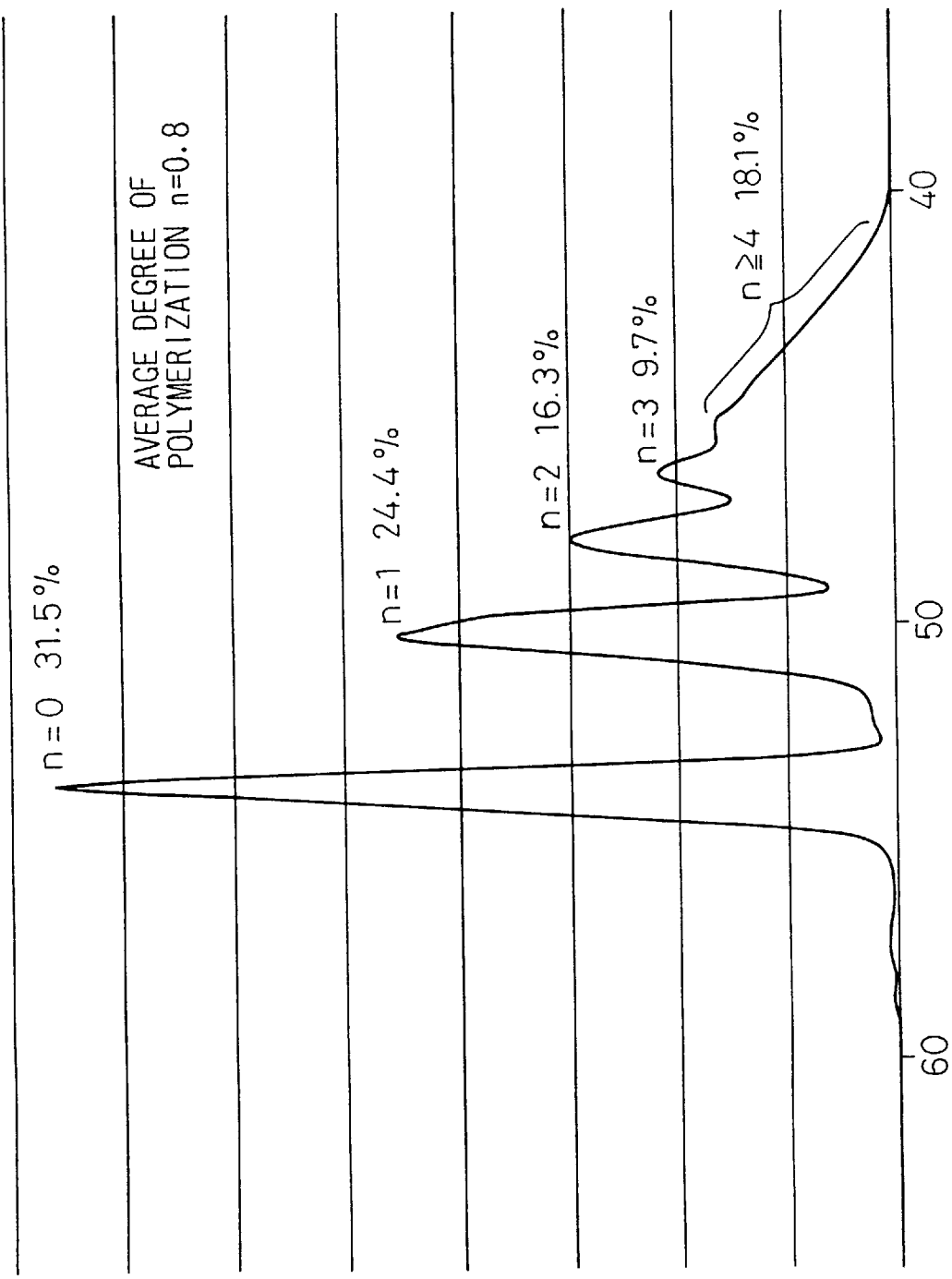

EPOXY RESIN COMPOSITIONS INCLUDING NOVEL PHENOL NOVOLAK CONDENSATES PRODUCED FROM BIS (METHOXYMETHYL)BIPHENYLS

This application is a division of application Ser. No. 08/530,735, filed Sep. 19, 1995, which application is entirely incorporated herein by reference now U.S. Pat. No. 5,612,442.

BACKGROUND OF THE INVENTION

1. Field of the Invention

The present invention relates to a bis(methoxymethyl) biphenyl useful as a starting material for a phenol novolak resin and an epoxy resin modifier, any mixtures of six isomers thereof, and processes for producing the same.

The present invention also relates to a novel phenol novolak condensate obtainable from a reaction between isomers of a bis(methoxymethyl)biphenyl or a mixture thereof and a phenol compound. This condensate is useful as a curing agent for an epoxy resin and a starting material for an epoxidized novolak resin, in addition to being useful for a thermosetting resin with a cross-linking agent such as hexamethylenetetramine.

2. Description of the Related Art

As an aromatic bis(methoxymethyl) derivative, there has been known in the past 1,4-bis(methoxymethyl)benzene. Phenol resins using this are disclosed in Japanese Examined Patent Publication (Kokoku) No. 47-13782, Japanese Examined Patent Publication (Kokoku) No. 47-15111, and Japanese Examined Patent Publication (Kokoku) No. 48-10960. However, a bis(methoxymethyl)biphenyl has not been known. Japanese Examined Patent Publication (Kokoku) No. 47-13782 and Japanese Examined Patent Publication (Kokoku) No. 47-15111 disclose that a bis(alkoxymethyl) biphenyl can be used for the production of phenol polymers. However, there were no examples of experiments actually using it for a phenol polymer.

Further, DE-2648701 discloses an example of the use of a 4,4'-isomer of bis(methoxymethyl)biphenyl as a component of a flame retardent improvement agent for polyvinyl chloride and an example of the synthesis of the same. According to this process, biphenyl is chloromethylated the biphenyl, followed by reacting with methanol in the presence of potassium hydroxide, then synthesizing bis (methoxymethyl)biphenyl. Since a 4,4'-isomer is produced at the chloromethylation stage, however, it is extremely difficult to synthesize a bis(methoxymethyl)biphenyl other than the 4,4'-isomer. Further, it is relatively easy to introduce a single chloromethyl group into biphenyl, but introducing two chloromethyl groups is hard. According to this reference, the reaction takes a long period of about 20 hours and further has a yield of about 60%.

Accordingly, a process for the production of a novel bis(methoxymethyl)biphenyl other than the 4,4'-isomer, and an industrially acceptable process for producing the same with a good yield of bis(methoxymethyl)biphenyl, including the 4,4'-isomer, have been sought.

Phenol novolak resins have been used as materials for brake pads etc. mixed with asbestos fibers and other fibrous fillers due to their low wearability, their good dimensional stability at high temperatures, and their good bonding ability, etc., but they have not necessarily been satisfactory in terms of heat resistance, etc.

Further, novolak epoxy resins obtained from a reaction of epoxy compounds with the phenol novolak resins, in particular, cresol novolak type epoxy resins, are inexpensive and are excellent in productivity, and therefore, these resins are widely used for semiconductor packages. These materials, however, sometimes have suffered from cracking, known as the "popcorn phenomenon," which accompanies rapid vaporization and expansion of the absorbed moisture at the time of solder reflow. Accordingly, a material having a low hygroscopicity and superior heat resistance has been sought. Improvement of the hygroscopicity and heat resistance is desired for the phenol novolak resins used as the curing agents of the epoxy resins as well.

As a method for solving the problem of heat resistance, it has been proposed in Japanese Examined Patent Publication (Kokoku) No. 47-13782, Japanese Examined Patent Publication (Kokoku) No. 47-15111, and Japanese Examined Patent Publication (Kokoku) No. 48-10960 to replace part or all of the formaldehyde with 1,4-bis(methoxymethyl) benzene or, in Japanese Unexamined Patent Publication (Kokai) No. 4-110317, it is proposed that bis (hydroxymethyl)benzene be reacted with a phenol compound to give a phenol polycondensate.

However, the epoxidated phenol resin obtained by this method is insufficient in heat resistance and is insufficient in improvement of hygroscopicity as well.

Further, a method for reducing the hygroscopicity property by an addition reaction of divinylbenzene instead of formaldehyde, with the phenol, followed by reacting with the epoxy compound has been disclosed in Japanese Unexamined Patent Publication (Kokai) No. 5-78457, but the result is not sufficient in terms of strength and low hygroscopicity.

Japanese Examined Patent Publication (Kokoku) No. 47-13782, Japanese Examined Patent Publication (Kokoku) No. 47-15111, and Japanese Unexamined Patent Publication (Kokai) No. 4-110317 disclose that it is possible to use bis(methoxymethyl) biphenyl or bis(hydroxymethyl) biphenyl to obtain a phenol polycondensate, but these publications make no specific disclosure of the invention of this application.

Further, Japanese Unexamined Patent Publication (Kokai) No. 5-117350 discloses a specific example of a 2:1 condensate of 2 molecules of phenol and 1 molecule of 4,4'-di(2-hydroxy-2-propyl)biphenyl. However, since this low molecular phenolic compound is crystalline and has a low melt viscosity, there is a problem that this compound is not easy to handle due to its large flowability during molding. On the other hand, this reference discloses that it is possible to use 4,4'-bis(methoxymethyl)biphenyl, but it does not specifically disclose the invention of this application.

SUMMARY OF THE INVENTION

Accordingly, the objects of the present invention are to eliminate the above-mentioned problems in the prior art and to provide a novel bis(methoxymethyl)biphenyl and a novel and effective production process thereof.

Other objects of the present invention are to provide novel phenol novolak condensates and a new application for use thereof.

In accordance with the present invention, there is provided a bis(methoxymethyl)biphenyl having the formula (I):

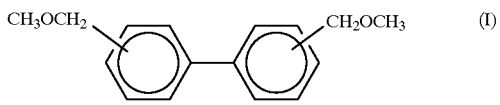

provided that the two CH₃OCH₂ groups are not positioned at the 4,4'-positions.

In accordance with the present invention, there is also provided a process for producing a bis(methoxymethyl) biphenyl having the formula (I'):

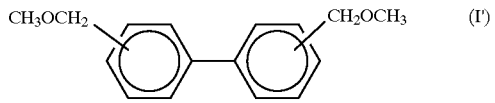

comprising effecting a dehalogenating coupling reaction of halogenated methoxymethylbenzene having the formula (II):

$$CH_3OCH_2-\bigcirc-X \quad (II)$$

wherein X is bromine, iodine or chlorine.

In accordance with the present invention, there is further provided a phenol novolak condensate obtainable from a reaction between an isomer of bis(methoxymethyl)phenyl having the above-defined formula (I') or a mixture thereof and a phenol compound.

BRIEF DESCRIPTION OF THE DRAWING

The present invention will be better understood from the description set forth below with reference to the accompanying drawings.

FIG. 12 is a GPC chart of the resin obtained in Example 2-6.

DESCRIPTION OF THE PREFERRED EMBODIMENTS

Figure 1:
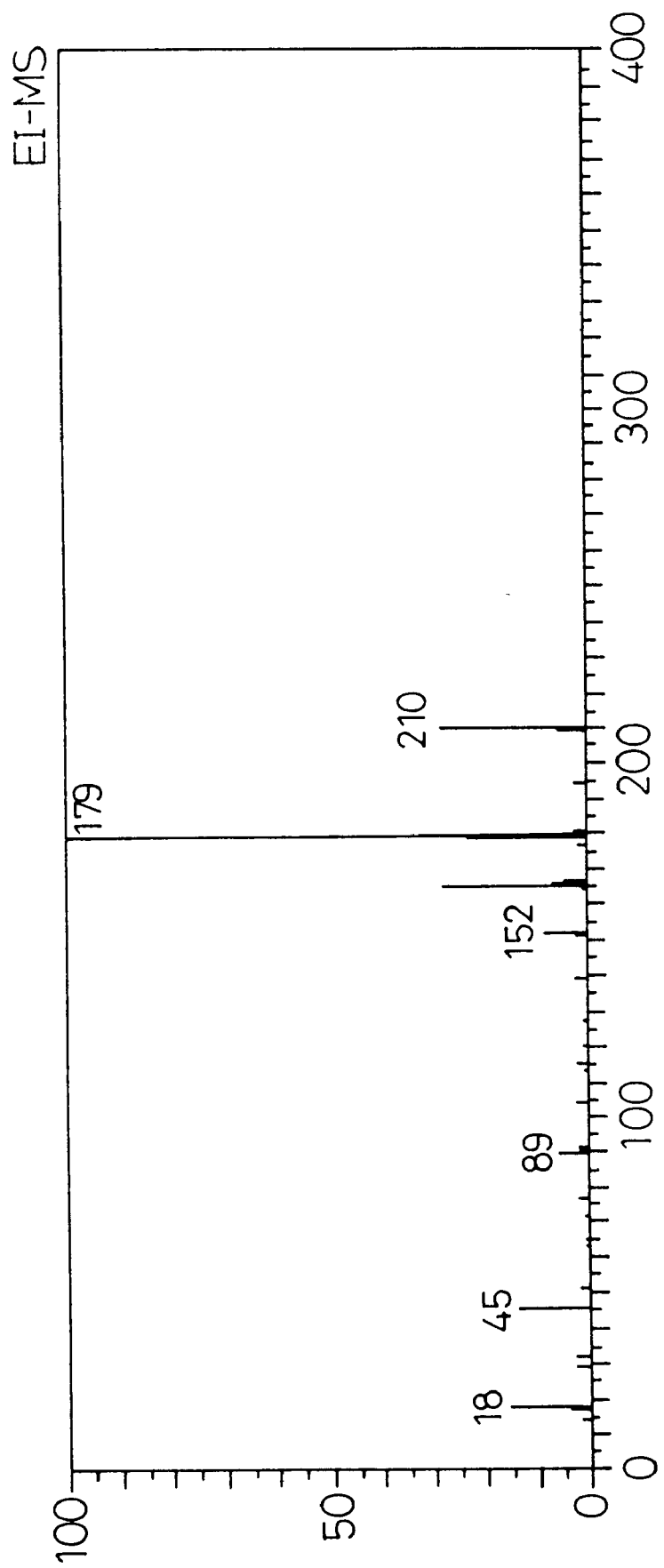
FIG. 1 is a mass analysis chart in Example 1-6.

The inventors engaged in repeated intensive studies on a process of production to obtain bis(methoxymethyl) biphenyl which is novel and for which there have been no effective means of synthesis and consequently, they discovered novel compounds serving as effective intermediates and, at the same time, established an economical, industrially practical process of synthesis of the same and thereby completed the first and second aspects of the present invention.

According to the present invention a novel phenol novolak condensate and new applications for use of the same are also provided. That is, the epoxy resin cured product obtained from a reaction of an epoxy resin with the present condensate, as a curing agent, and the epoxy resin cured product obtained from a reaction of an epoxy resin curing agent with the epoxidized novolak resin obtained from the epoxidation of the present condensate exhibit extremely superior properties in terms of hygroscopicity, heat resistance, and pliability. The novel phenol novolak condensate according to the present invention and the epoxidized resins obtained therefrom have advantageous characteristics such as preferable molecular weight distribution and the small generation of flashes (or burrs) during the molding, and therefore, the productivity can be improved. Further, the phenol resin cured product obtained by curing the present condensate using hexamethylenetetramine or other curing agents for phenol resins exhibits extremely superior properties, in terms of wear resistance, dimensional stability at high temperatures, and bonding properties.

As mentioned above, the bis(methoxymethyl)biphenyl according to the present invention has the above-specified formula (I), except 4,4'-bis(methoxymethyl)biphenyl. The general formula (I') specifically includes the six types of bis(methoxymethyl)biphenyl of formulas (Ia) to (If).

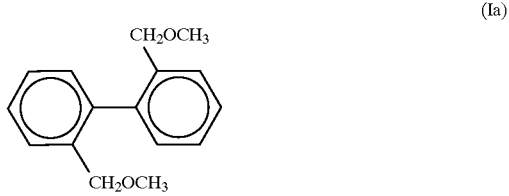

(Ia)

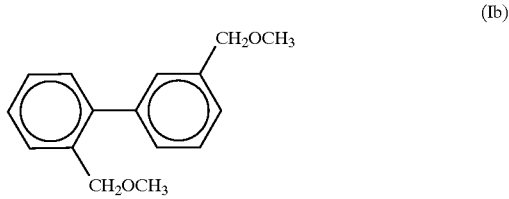

(Ib)

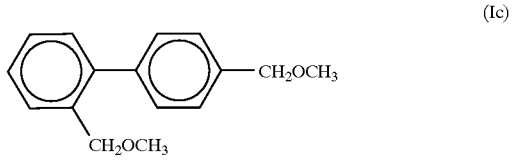

(Ic)

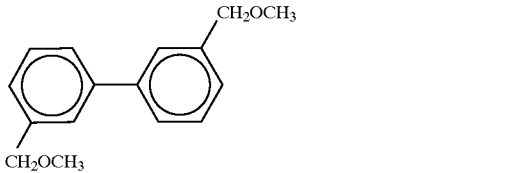

(Id)

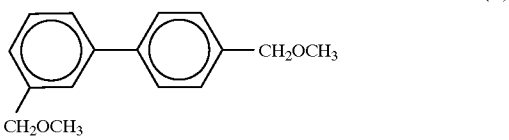

(Ie)

-continued

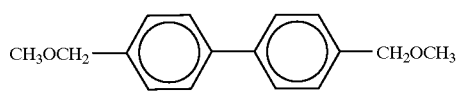
(If)

Further, the present invention relates to a mixture containing isomers of the bis(methoxymethyl) biphenyl of the above general formula (I') wherein the total of the content of the 2,4'-isomer of the formula (Ic) and the content of the 4,4'-isomer of the formula (If) is at least 40% by weight. Preferably, it relates to a mixture wherein the content of the 2,4'-isomer is at least 40% by weight and the content of the 4,4'-isomer is at least 40% by weight.

Further, the present invention relates to a process for producing the bis(methoxymethyl)biphenyl having the general formula (I') by effecting a dehalogenating coupling reaction of the halogenated methoxymethylbenzene having the general formula (II). The present invention in particular is a process suited to the production of the 2,2'-isomer, 2,4'-isomer, or 4,4'-isomer and is suited to the production of a mixture of a total content of the 2,4'-isomer and 4,4'-isomer of at least 40% by weight or a mixture of a content of the 2,4'-isomer of at least 40% by weight and a content of the 4,4'-isomer of at least 40% by weight.

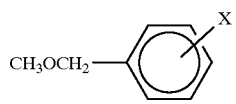
(II)

wherein, X is bromine, iodine, or chlorine.

The bis(methoxymethyl)biphenyl according to the present invention may be synthesized by the following process:

(Process 1)

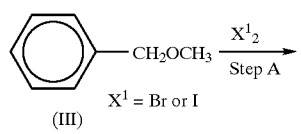
(III)
$X^1$ = Br or I

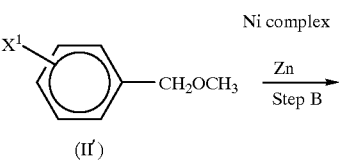
(II')

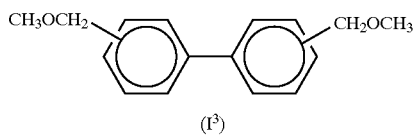
(I³)

(Process 2)

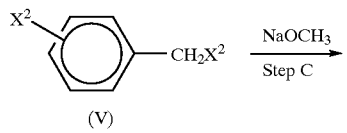
(V)
$X^2$ = Cl

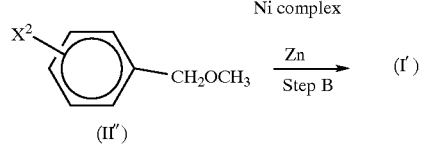
(II')

(Process 3)

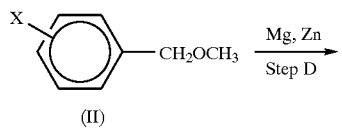
(II)
X = Br, I or Cl

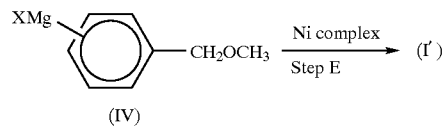
(IV)

First, the process for synthesis of the intermediate halogenated methoxymethylbenzene will now be explained.

Process of Synthesis of methoxymethyliodobenzene (Step A of Process 1):

In the case of an iodide isomer, a mixture of the starting material methoxymethylbenzene, iodine, iodic acid, a catalyst, and a solvent is prepared by heating and stirring these components at a temperature of 50° to 100° C. The amounts of the iodine and the iodic acid used are ¼ to ½ mole based upon 1 mole of the starting material. In particular, ⅓ to ½.₅ mole is suitable. If the amounts of these components are too small, 100% of the starting material is not consumed, while if the amounts are too large, unpreferable byproducts such as diiodide isomers etc., are produced.

The acid catalyst used in the above step is preferably a protonic acid. In particular, nonvolatile acids such as sulfuric acid and p-toluene sulfonic acid, are particularly preferred. The amount used is suitably ⅕ to ¹/₃₀ mole, especially ½ to ¹/₁₅ mole, based upon 1 mole of the starting material. If the amount of the acid catalyst is too small, the reaction rate becomes slow, while if it is too large, there is sometimes a problem with a rapid reaction occurring.

The solvent used in the present invention is a fatty acid type solvent such as acetic acid or propionic acid. Acetic acid is particularly preferred. The fatty acid type solvent may be used alone or in any mixture thereof, and it may be mixed with low boiling point hydrocarbons, such as n-hexane and n-octane and halogenated hydrocarbons, such as chloroform and dichloromethane.

The reaction is preferably carried out within a range of 40° to 120° C., particularly suitably within a range of 60° to 90° C. If the temperature is low, the reaction speed is slow, and when high, various byproducts are produced. The reaction time is preferably within a range of 3 to 12 hours, particularly suitably within a range of 5 to 8 hours.

In this method for obtaining an iodide isomer, the methoxymethyliodobenzene which is normally obtained is a mixture of o-, m-, and p-isomers of the formulas (IIa) to (IIc). The proportions of these change according to the type of the halogen used and the reaction conditions, but normally a mixture of o-:m-:p-isomers of 1:(0.2 to 0.4):(2 to 4) is obtained.

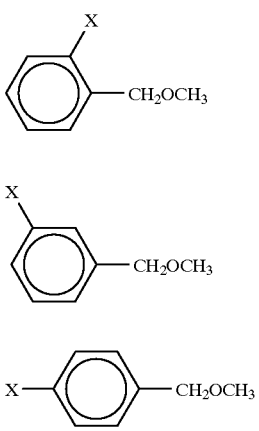

A specific isomer selected from the o-, m-, and p-isomers of the methoxymethyliodobenzene may be obtained by separation of the mixture obtained by the above reaction by normal separation methods such as distillation.

Method of Synthesis of Methoxymethylbromobenzene (Step A of Process 1):

A bromide isomer may be obtained by dropwise adding bromine to a mixture of methoxymethylbenzene and a solvent such as dichloromethane at 0° to 25° C. (see: e.g., Journal of the Chemical Society (JCS), 36, 1941)

Even in this method for obtaining a bromide isomer, the methoxymethylbromobenzene is normally obtained as a mixture of the o-, m-, and p-isomers of the formulas (IIa) to (IIc). The proportions of the mixture will vary according to the type of the halogen used and the reaction conditions, but normally a mixture of o-:m-:p-isomers=1:(0.2 to 0.4):(2 to 4) is obtained.

A specific isomer selected from the o-, m-, and p-isomers of the methoxymethylbromobenzene may be obtained by separation of the mixture obtained by the above reaction by other normal separation methods such as distillation.

Method of Synthesis of Methoxymethylchlorobenzene (Step C of Process 2):

A chloride isomer may be synthesized by reacting a p- or o-chlorobenzyl chloride or mixtures thereof with $NaOCH_3$ in a solvent such as methanol at 40° to 90° C. to cause etherification.

Next, the synthesis of bis(methoxymethyl)biphenyl by a coupling reaction of halogenated methoxymethylbenzene will now be explained.

If a halogenated methoxymethylbenzene or a mixture of the three types of isomers thereof are reacted in accordance with step B in the presence of a nickel complex and a metal in a solvent, the dehalogenating coupling reaction occurs to thereby give bis(methoxymethyl) biphenyl.

The nickel complexes used herein are pyridine based complexes, such as bipyridyl nickel dichloride and bispyridine nickel dichloride, or phosphine based complexes, such as triphenylphosphine nickel dichloride, bisdiphenylphosphinoethane nickel dichloride, etc. Particularly preferred are pyridine based complexes, especially bipyridyl nickel dichloride.

Here, the amount of the nickel complex used is 1/100 to 1 mole, preferably 1/15 to 1/50 mole, per mole of the halogenated methoxymethylbenzene. If the amount thereof is too small, the starting material is not completely consumed, while if it is too large, there is the problem of lack of economy.

As the metal, zinc, manganese, and magnesium may be used. These metals are preferably used in the ordinary powder form. The amount used is 0.5 to 2 moles, preferably 0.55 to 1 mole, per mole of the halogenated methoxymethylbenzene. If the amount thereof is too small, the starting material is not consumed, while if it is too large, the reaction mixture becomes slurry and is difficult to handle and, further, there is the problem of a lack of economy.

The solvent used may be a solvent used for an ordinary coupling reaction as described in J. Org. Chem. 51, 2627 (1986); the Bull. Chem. Soc. Jpn., 63, 80 (1990), etc., that is, aprotonic polar solvents such as dimethylacetamide (DMAc) or dimethylformamide (DMF). However, in a dehalogenating coupling reaction of a halogenated methoxymethylbenzene, a large amount of byproducts are produced, and in many cases, the process cannot be said to be industrially advantageous.

Thus, the present inventors engaged in detailed studies on dehalogenating coupling reactions and, as a result, found that the results of the reaction differ tremendously depending upon the combination of the type of the solvent and the metal used.

That is, if 1,3-dimethyl-2-imidazolidinone (DMI) and zinc powder, DMAc and manganese powder, DMF and manganese powder, and other combinations are used, it is possible to obtain the desired isomers of the bis (methoxymethyl)biphenyl and their mixtures under moderate reaction conditions and at a high yield.

Further, it is preferable to perform the dehalogenating coupling reaction by heating a mixture of nickel complex and metal powder at a temperature of 100–200° C. under a reduced pressure of 2 to 10 mmHg or under a nitrogen atmosphere, then adding the halogenated methoxymethylbenzene and a solvent. In the various solvent-metal powder systems, it is possible to obtain the desired product at a high yield and, at the same time, the amounts of the catalyst, metal powder, and solvent used can be reduced to ½ to ⅓ compared with the amounts used shown in the abovementioned J. Org. Chem., 51, (1986), 2627 etc.

As a result, an industrial and economical process for the production of various types of bis(methoxymethyl) biphenyl isomers and their mixtures through a dehalogenating coupling reaction of a halogenated methoxymethylbenzene using a nickel-complex-metal powder catalyst system can be established.

This coupling reaction is suitably performed normally at a range of 50° to 200° C., particularly 70° to 180° C., for about 1 to 8 hours.

Further, the coupling may be performed by the following method:

First, as shown by step D, an ordinary method is followed to effect a reaction between the halogenated methoxymethylbenzene and metal magnesium or metal zinc to convert to a corresponding Grignard reagent.

Next, step E is followed to perform the dehalogenating coupling reaction in the presence of a metal complex of nickel, cobalt, etc.

The proportion of the six types of isomers obtained at this step is, in the method using either of Zn or Mg, Ia:Ib:Ic:Id:Ie:If=1:(0.2 to 0.6):(4 to 7):(0.01 to 0.1):(0.5 to 2.0):(5 to 15).

After the above coupling reaction, the inorganic substances are removed from the reaction solution, then distillation or recrystallation procedures are used to obtain the bis(methoxymethyl)biphenyl. At this step, by performing precision distillation or careful recrystallization, it is possible to separate the solution into a number of components whereby mixtures of isomers in accordance with the present invention can be obtained.

In the present invention, the proportions of production of the 2,2'-isomer, 2,4'-isomer, and 4,4'-isomer are large, and therefore, the present invention is particularly suited to the production of these isomers.

Further, to more efficiently produce specific isomers of the bis(methoxymethyl)biphenyl, it is particularly preferable to use specific isomers as the starting materials used for the coupling reaction, that is, the halogenated methoxymethylbenzene. For example, to produce 4,4'-bis(methoxymethyl)biphenyl, a p-methoxymethylhalobenzene can be used as the starting material.

As mentioned above, the third embodiment of the present invention relates to a phenol novolak polycondensate obtained from a reaction between a phenol compound and the isomers of the bis(methoxymethyl)biphenyl of the above-specified formula (I) or mixtures thereof.

The phenol compound usable in the present invention means a compound having at least one phenolic hydroxyl group at its aromatic ring.

Specific examples of such phenol compounds include unsubstituted phenols such as phenol, resorcinol, and hydroquinone; single substituted phenols such as cresol, ethylphenol, n-propylphenol, iso-propylphenol, t-butylphenol, octylphenol, nonylphenol, and phenylphenol; double substituted phenols such as xylenol, methylpropylphenol, methylbutylphenol, methylhexylphenol, dipropylphenol, dibutylphenol, guaiacol, and catechol ethyl ether; triple substituted phenols such as trimethylphenol; naphthols such as naphthol, and methylnaphthol; and bisphenols such as bisphenol, bisphenol A, and bisphenol F.

The isomers of the bis(methoxymethyl)biphenyl having the formula (I) specifically are the compounds of the above-mentioned structural formulas (Ia) to (If). These isomers may be used in any mixtures thereof.

Further, 4,4'-bis(methoxymethyl)biphenyl may be obtained by chloromethylating biphenyl, and then etherifying with sodium methoxide.

The phenol novolak condensate according to the present invention is obtained by effecting a reaction between isomers of bis(methoxymethyl)biphenyl or mixtures thereof and a phenol compound in the presence of an acid catalyst for 1 to 7 hours while demethanolating.

In this reaction, the proportion of the phenol compound and the bis(methoxymethyl)biphenyl mixture to be used is preferably within a range of 1:0.1 to 1. If the proportion is less than 0.1, a large amount of unreacted phenol has to be removed, whereby the process is made uneconomical. Further, if the proportion is more than 1, gelation occurs which is not desirable for a practical resin.

As the acid catalyst used in this reaction, p-toluenesulfonic acid, sulfuric acid, dimethylsulfuric acid, diethylsulfuric acid, etc. may be mentioned. The amount used is preferably $\frac{1}{10}$ to $\frac{1}{100}$ mole per 1 mole of the phenol. If the amount is too small, the reaction rate becomes slow, while if it is too large, there is sometimes a problem with a rapid reaction occurring and an inability to control the reaction.

The reaction temperature is preferably 120° to 190° C. If the temperature is low, the reaction speed becomes slow, while if it is high, there is sometimes a problem such as gelation.

The phenol novolak condensate obtained in this way has the structure as shown in the general formula (III). Depending upon the type of the phenol compound used, there is a substituent on the phenol ring.

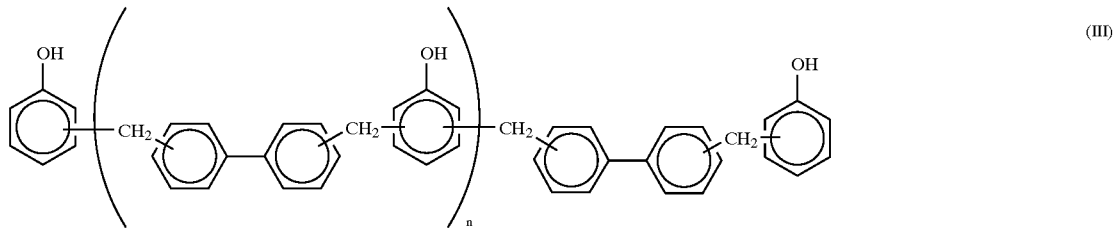

(III)

Among these, the 2,4'-isomer shown by formula (Ic), the 4,4'-isomer shown by formula (If), and a mixture of isomers containing at least 5% by weight of 2,4'-isomers and at least 40% by weight of 4,4'-isomers are preferable. In particular, mixtures of isomers containing at least 5% by weight of 2,4'-isomer and at least 40% by weight of the 4,4'-isomer are preferable. mixtures of isomers containing at least 10% by weight of 2,4'-isomer and at least 40% by weight of 4,4'-isomer are the most preferable. Since the 2,4'-isomer is effective for increasing the breakage energy of cured epoxy resins, a cured epoxy resin having excellent mechanical properties can be obtained when a phenol novolak condensate obtained from a mixture containing 2,4'-isomer is used.

These bis(methoxymethyl)biphenyl isomers and mixtures thereof may be obtained by effecting a dehalogenating coupling reaction of a halogenated methoxymethylbenzene. The proportion of the isomers in the reaction product generally is Ia:Ib:Ic:Id:Ie:If=(1):(0.2 to 0.6):(4 to 7):(0.01 to 0.2):(0.5 to 2.0):(5 to 15), but it is possible to obtain a specific isomer or a specific mixture of isomers by selecting the starting materials and the reaction conditions.

Here, n differs according to the reaction conditions, but normally is an integer of 0 to 9. When n=0, the molten viscosity is small, and therefore, the compound easily flows during molding and is not practical. Accordingly, for practical use, a mixture containing 50% by weight or more, preferably 60% by weight or more, of the condensate having n of 1 or more is preferable.

Next, the use of the phenol novolak condensate as a curing agent for epoxy resins will now be explained.

Since the phenol novolak condensate has a phenolic hydroxyl group, in the same way as with normal phenol novolak resins, the phenol novolak condensate can be used as a curing agent for epoxy resins. The cured product resulting from the use of this phenol novolak polycondensate as a curing agent is superior in hygroscopicity, heat resistance, and pliability.

Examples of the epoxy resin usable in this curing step are bisphenol diglycydyl ether type epoxy resins which impart epoxy groups to a bisphenol such as bisphenol A or bisphenol F; novolak type epoxy resins imparting epoxy groups to a phenol novolak type resin such as normal phenol novolak resins, o-cresol novolak resins and brominated phenol novolak resins; diphenylmethanediaminetrtraglycidyl ether, cyclohexanediaminetetraglycidyl ether, and other glycidylamine type epoxy resins; polyethylene glycol diglycidyl ether, epoxidized SBR, epoxidized soybean oil, and other fatty acid epoxy resins; dihydroxybiphenyldiglycidyl ether type epoxy resins imparting epoxy groups to a dihydroxybiphenyl such as 4,4'-dihydroxybiphenyl, 3,3',5,5'-tetramethyl-4,4'-dihydroxybiphenyl; 1,6-dihydroxynaphthalenediglycidyl ether and other condensation multi-ring aromatic type epoxy resins. Among these, novolak type epoxy resins, dihydroxybiphenyldiglycidyl ether type epoxy resins and condensation multi-ring aromatic type epoxy resins are preferred, and in particular a novolak type epoxy resin is preferred.

To obtain an epoxy resin cured product using the phenol novolak condensate of the present invention as a curing agent, the phenol novolak condensate of the present invention and the above said epoxy resin are mixed so that the ratio of the hydroxyl groups of the phenol novolak condensate of the present invention and the epoxy groups of the epoxy resin becomes generally equal and the resultant epoxy resin composition is heated at about 100° to 250° C. In this reaction, it is preferable to add to the epoxy resin composition a curing promotor generally used for promoting curing, for example, N-methylimidazole, triethylamine, triphenylphosphine, etc. Further, optionally or if desired, it is also possible to add a filler, coupling agent, flame retardant, lubricant, mold release agent, plasticizer, coloring agent, thickener, and other various types of additives.

Next, the application of the phenol novolak polycondensate as a starting material for an epoxy resin will now be explained.

The phenol novolak condensate of the present invention may be made into an epoxidized novolak resin by epoxidation. This epoxidized novolak resin, for example, includes a novolak type epoxy resin of the formula (IV) obtained by causing a reaction of the phenol novolak condensate of the present invention with epichlorohydrin or other epihalohydrins in the presence of an alkali, novolak polycondensate of the present invention), urea resins, melamine resins, etc. may be mentioned. Among these, ordinary phenol novolak resins, o-cresol novolak resins, brominated phenol novolak resins, and other phenol novolak resins, including the phenol novolak condensate of the present invention, are preferred. Especially, the best results can be achieved when the epoxidized novolak resin of the present invention is cured with the phenol novolak condensate of the present invention as a curing agent.

To obtain the cured product of the epoxidized novolak resin of the present invention, it is possible, as with the curing method mentioned above, to obtain the epoxy resin composition and then heat it. Further, there is the similarity that it is possible to add curing promoters and other additives.

Next, the use of the phenol novolak condensate of the present invention as a starting material for a phenol resin (cured product) will be explained.

To obtain a cured product of a phenol resin using the phenol novolak condensate of the present invention, the phenol novolak condensate of the present invention and hexamethylenetetramine, formaldehyde, or other curing agents for phenol resins are mixed to make the phenol resin composition which is then heated at about 80 to 200° C., preferably 150° C. to 180° C. to cure it.

If desired, it is also possible to add, to the phenol resin composition and phenol resin (cured product), a filler, coupling agent, flame retardant, lubricant, mold release agent, plasticizer, coloring agent, thickener, and other various types of additives. The phenol resin (cured product) thus obtained is superior in wear resistance, dimensional stability at high temperatures, and bonding.

As explained above, the resin obtained by using the phenol novolak condensate of the present invention as a curing agent for an epoxy resin can be used as an adhesive, paint, sealing material, friction material, grindstone, etc. and has superior properties in terms of heat resistance, closeness of adhesion, water absorption property, and mechanical properties.

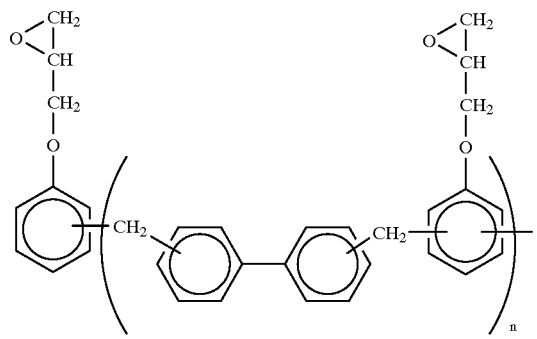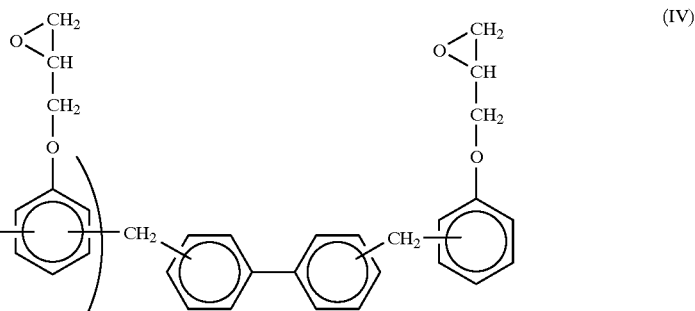

wherein, n is an integer of from 0 to 9. Further, there may be a substituent on the phenol ring depending on the type of the phenol compound used as the starting material for the phenol novolak condensate.

The epoxidized novolak resin of the present invention may be cured with various types of curing agents. The cured product of the epoxy resin, like with the epoxy resin mentioned above, is superior in hygroscopicity, heat resistance, and pliability.

As the curing agent for an epoxy resin in this reaction, various types of amines, polycarboxylic acids and their anhydrides, phenol novolak resins (including the phenol Further, a resin obtained by curing the phenol novolak condensate using hexamethylenetetramine or aldehydes may also be used as an adhesive, paint, sealing material, friction material, grindstone, etc. and has superior properties in terms of heat resistance, closeness of adhesion, water absorption property, and mechanical properties.

Further, a resin with superior properties is obtained even when adding to the phenol novolak resin and epoxidated novolak resin obtained in the present invention carbon black or other pigments, asbestos, silica, talc, and other fillers, glass fibers, rock wool, cotton, and other reinforcing materials, etc.

EXAMPLES

The present invention will now be explained in more detail by, but by no means limited to, the following Examples.

Example 1-1

Iodination of Methoxymethylbenzene

Into a solution of 146.5 g (1.20 moles) of methoxymethylbenzene, 300 ml of acetic acid, and 80 ml of n-hexane 101.5 g (0.40 mole) of iodine, 70.3 g (0.40 mole) of iodic acid, and 4 ml of sulfuric acid were added, then the mixture was stirred at 80° C. for 5 hours. 600 ml of n-hexane and 700 ml of water were then added to the reaction solution, which was then shaken well, then the n-hexane layer was separated, washed, and dried. The solvent was distilled off, the solution was then distilled under reduced pressure to obtain 216.5 g (0.87 mole) of a mixture of the three types of isomers of methoxymethyliodobenzene.

Boiling point: 93° to 96° C./4 mmHg

Gas chromatography (column: Apiezon Grease L 10% on Uniport 2 m) gave two peaks (ratio of peak areas: 1:3). However, the results of $^{13}$C-NMR measurement showed the presence of the m-isomer in addition to the o-isomer and the p-isomer. Based on these results, the isomers in the composition were found from $^1$H-NMR to be o-isomer:m-isomer:p-isomer=1:0.25:2.8.

Example 1-2

Bromination of Methoxymethylbenzene

Into a mixture of 12.2 g (0.1 mole) of methoxymethylbenzene, 8.2 g (0.1 mole) of sodium acetate, and 100 ml of dichloromethane 12.0 g (75 mmole) of $Br_2$ was added dropwise over 3 hours at room temperature. Next, the solution was raised to 60° C. and the reaction was continued for a further 3 hours. After the end of the reaction, an aqueous solution of sodium sulfite was added to deactivate the remaining bromine, then the dichloromethane layer was separated by a liquid separation procedure. This was washed with water and dried, then analyzed by gas chromatography, whereby it was found that 18.3 g (91 mmole) of a mixture of three types of isomers of methoxymethylbromobenzene was obtained. The proportions of the isomers in the composition were o-isomer:m-isomer:p-isomer=1:0.20:3.8

Example 1-3

Deiodo-coupling of Methoxymethyliodobenzene

A mixture comprised of 174.3 g (0.70 mole) of the methoxymethyliodobenzene obtained in Example 1-1 (mixture of three types of isomers), 14.2 g (46.7 mmole) of bipyridyl nickel dichloride (Ni(bipy)Cl$_2$.H$_2$O), 50.4 g (0.77 g atom) of zinc powder, 9.2 g (0.117 mole) of pyridine, and 350 ml of DMI was stirred vigorously at 90° C. for 5.5 hours. After the end of the reaction, the solids were removed by suction filtration and the majority of the solvent was removed by distillation under reduced pressure. The residue was cooled, then a 5% aqueous solution of hydrochloric acid was added to the residue, which was then sufficiently mixed and separated. The oily layer portion was further washed with water and the remaining small amount of solvent was distilled off under reduced pressure. The residue was analyzed by gas chromatography (SE-30, 5%, 2 m, 120° to 230° C.), as a result of which it was found that 80.3 g (0.332 mole) of a mixture of six isomers of bis(methoxymethyl)biphenyl was obtained.

The proportions of the isomers were 2,2'-:2,3'-:2,4'-:3,3'-:3,4'-:4,4'=1:0.5:5.5:0.08:0.3:7.5

Example 1-4

Debromo-coupling of Methoxymethylbromobenzene 20.1 g (0.10 mole) of the methoxymethyl-bromobenzene mixture obtained in Example 1-2, 2.04 g (6.7 mmole) of Ni(bipy)Cl$_2$.H$_2$O, 7.19 g (0.11 g atom) of zinc powder, 1.32 g (16.7 mmole) of pyridine, and 50 ml of DMI were stirred vigorously at 90° C. for 5.5 hours. After the end of the reaction, the same post-treatment and analysis were performed as in Example 1-3, whereby 11.5 g (47.5 mmole) of a mixture of six isomers of bis(methoxymethyl)biphenyl was obtained.

The proportions of the isomers were 2,2'-:2,3'-:2,4'-:3,3'-:3,4'-:4,4'-=1:0.4:7.6:0.04:1.3:14.2

Example 1-5

Dechloro-coupling of Methoxymethylchlorobenzene 30.4 g (0.1 mole) of Ni(bipy)Cl$_2$.H$_2$O and 90.5 g (1.65 g atom) of manganese powder were taken up in a 3-liter four-necked flask equipped with a cooling tube, gas introduction tube, and stirring device. This was heated at 100° C. for 1 hour under the flow of nitrogen gas.

Next, a mixture of 352.1 g (2.25 mole) of p-methoxymethylchlorobenzene, 117.4 g (0.75 mole) of o-methoxymethylchlorobenzene, and 1.5 liters of DMAc was added to the above four-necked flask. The mixture was then vigorously stirred at 120° C. to cause a reaction for 3 hours.

The solution was cooled to room temperature, then the solids were filtered out and the filtrate was distilled under reduced pressure to thereby distill off the DMAc. 400 ml of a 3 percent aqueous solution of hydrochloric acid was added to the residue, the mixture was sufficiently stirred, then the precipitate was filtered out. The filtrate was successively washed by 250 ml of 3% aqueous solution of sodium carbonate and 250 ml of water and the oily layer portion was distilled under reduced pressure at 200° C. and 3 Torr to obtain 328.4 g (1.36 mole) of the 154° to 174° C. fraction. This liquid was measured by gas chromatography, whereupon it was found that the purity was 99.6% and the yield of the desired substance was 90.0%.

The proportions of the isomers were 2,2'-:2,4'-:4,4'-=0.2:42.6:55.8

Example 1-6

Synthesis of 2,2'-bis(methoxymethyl)biphenyl by Dechloro-coupling of o-Methoxymethylchlorobenzene 10.03 g (33 mmole) of Ni(bipy)Cl$_2$.H$_2$O and 30.1 g (0.55 g atom) of manganese powder were taken up in a 300-ml four-necked flask equipped with a cooling tube, gas introduction tube, and stirring device. This was heated at 120° C. for 1 hour under the flow of nitrogen gas.

Next, a mixture of 156.6 g (1.00 mole) of o-methoxymethylchlorobenzene and 300 ml of DMAc was added to the above four-necked flask. The mixture was then vigorously stirred at 120° C. to cause a reaction for 5 hours.

The solution was cooled to room temperature, then the solids were filtered out and the filtrate was distilled under reduced pressure to thereby distill off the DMAc. 100 ml of toluene and 130 ml of a 3% aqueous solution of hydrochloric acid was added to the residue, the mixture was sufficiently stirred, then the precipitate was filtered out. The precipitate was washed with 100 ml of toluene, the filtrate and the washings were combined, and successive washing was performed by 130 ml of 3% aqueous solution of sodium carbonate and 200 ml of water. The toluene layer was distilled under reduced pressure to obtain a residue which was recrystallized by n-hexane to obtain 105.4 g (0.435 mole) of 2,2'-bis(methoxymethyl)biphenyl as a white solid. The purity was 99.5% and the yield of the desired substance was 86.5%.

The results of element analysis were

H:C=7.58:79.06

The mass analysis (EI) was as shown in FIG. 1.

Figure 2:
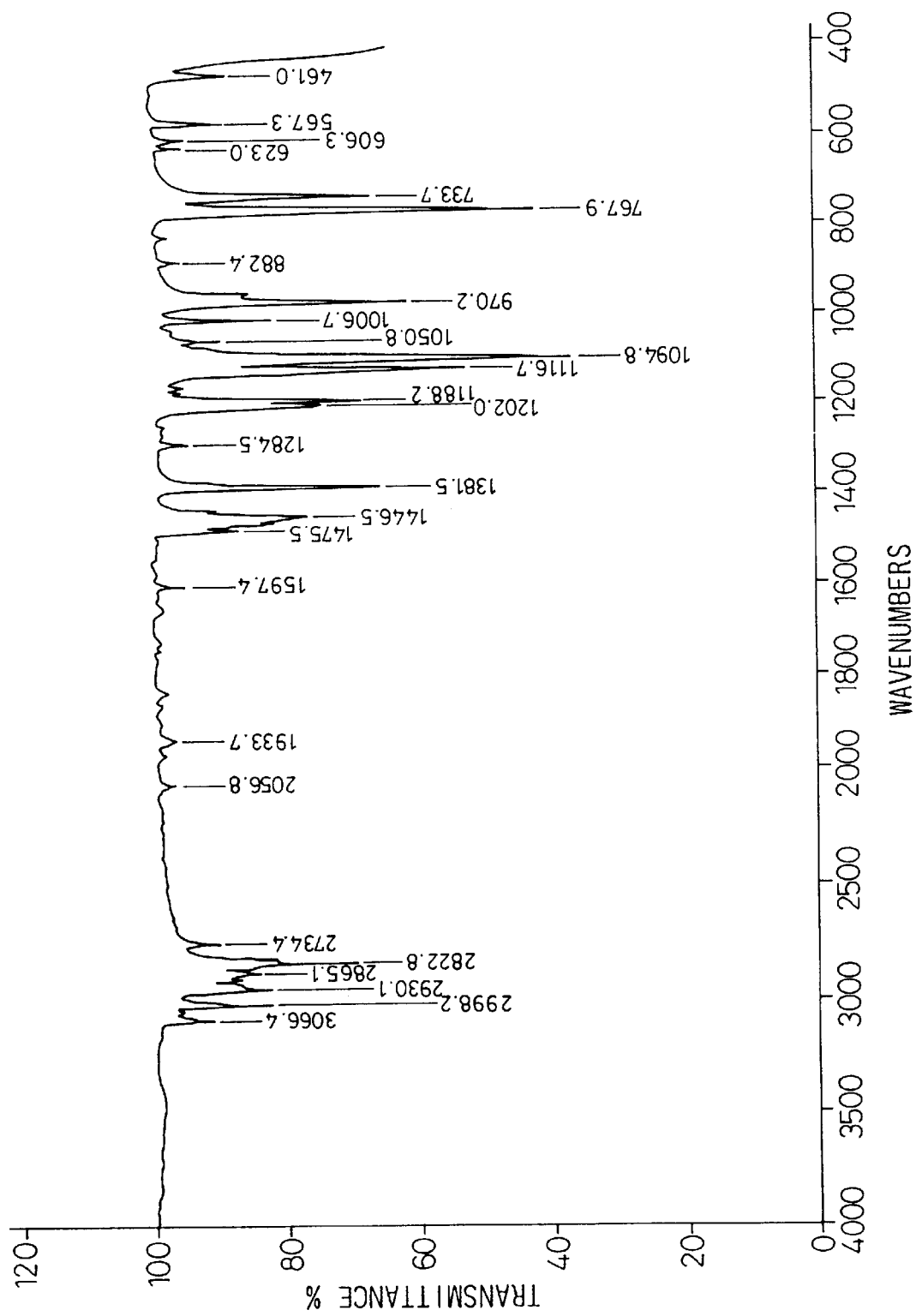
FIG. 2 is an infrared absorption spectrum in Example 1-6.

The infrared absorption spectrum was as shown in FIG. 2.

Figure 3:
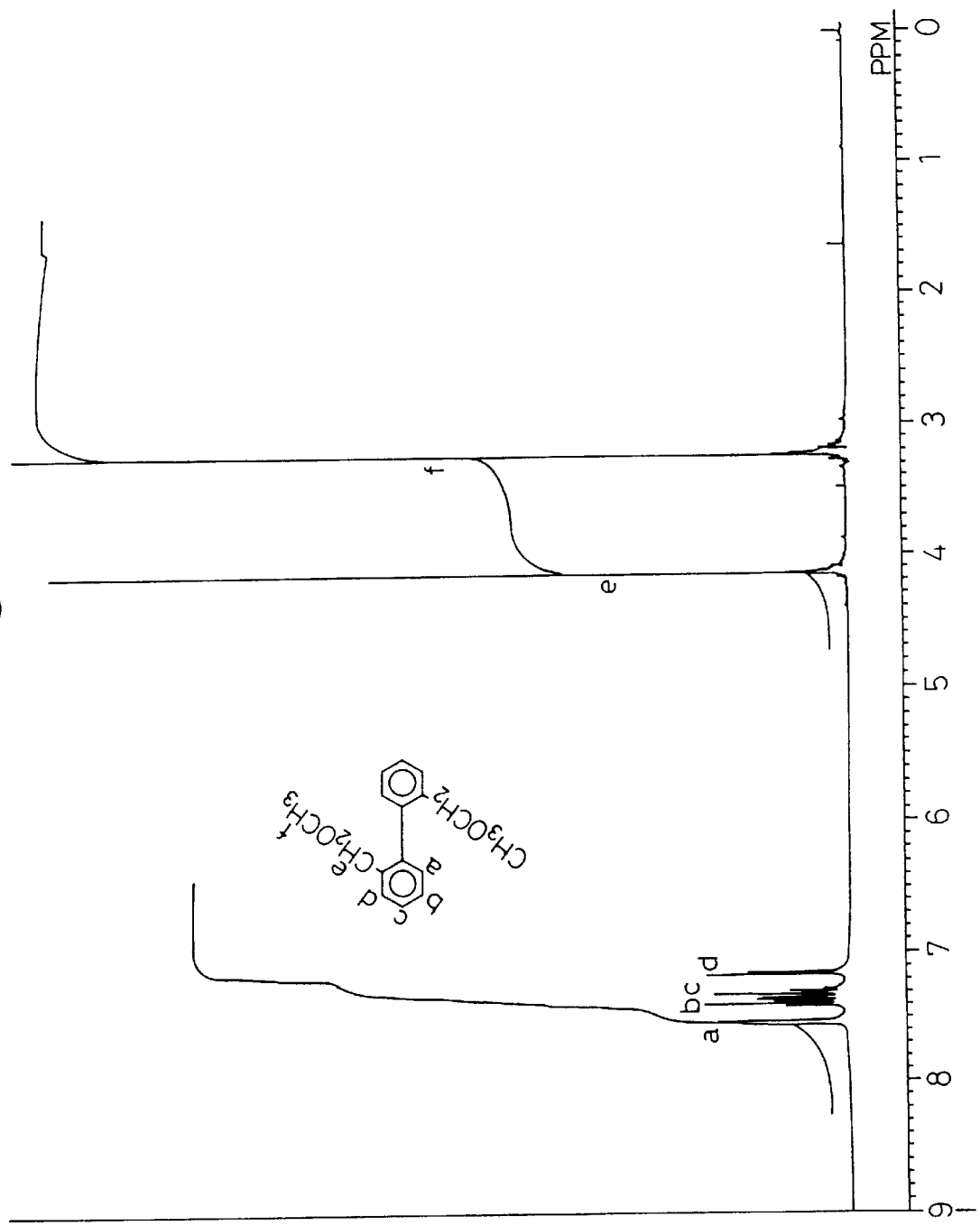
FIG. 3 is a result of ¹H-NMR obtained in Example 1-6.

The results of the $^1$H-NMR (solvent: CDCl$_3$) were as shown in FIG. 3.

Example 1-7

Synthesis of 4,4'-bis(methoxymethyl)biphenyl by Dechloro-coupling of p-Methoxymethylchlorobenzene 1.43 g (5 mmole) of Ni(bipy)Cl$_2$.H$_2$O and 4.62 g (0.0824 g atom) of manganese powder were taken up in a 100-ml four-necked flask equipped with a cooling tube, gas introduction tube, and stirring device. This was heated at 100° C. for 1 hour under a reduced pressure of 5 Torr.

Next, the mixture was cooled to room temperature, then a mixture of 23.49 g (150 mmoles) of p-methoxymethylchlorobenzene and 52 ml of DMAc was added to the above four-necked flask. The mixture was then vigorously stirred at 120° C. to cause a reaction for 3 hours.

The solution was cooled to room temperature, then the solids were filtered out, and the filtrate was distilled under reduced pressure to thereby distill off the DMAc. 20 ml of a 3% aqueous solution of hydrochloric acid was added to the residue, the mixture was sufficiently stirred, then the precipitate was filtered out. The filtrate was successively washed by 20 ml of 3% aqueous solution of sodium carbonate and 20 ml of water. The oily layer portion was subjected to evaporation under reduced pressure at 200° C. and 3 Torr to obtain 17.82 g (73.6 mmole) of the fraction at 170° to 174° C., whereby 4,4'-bis(methoxymethyl)biphenyl was obtained. This was a solid at room temperature. Analysis by gas chromatography showed its purity was 98.7%. The yield of the desired substance was 96.8%.

The results of element analysis were

H:C=7.52:79.34

Figure 4:
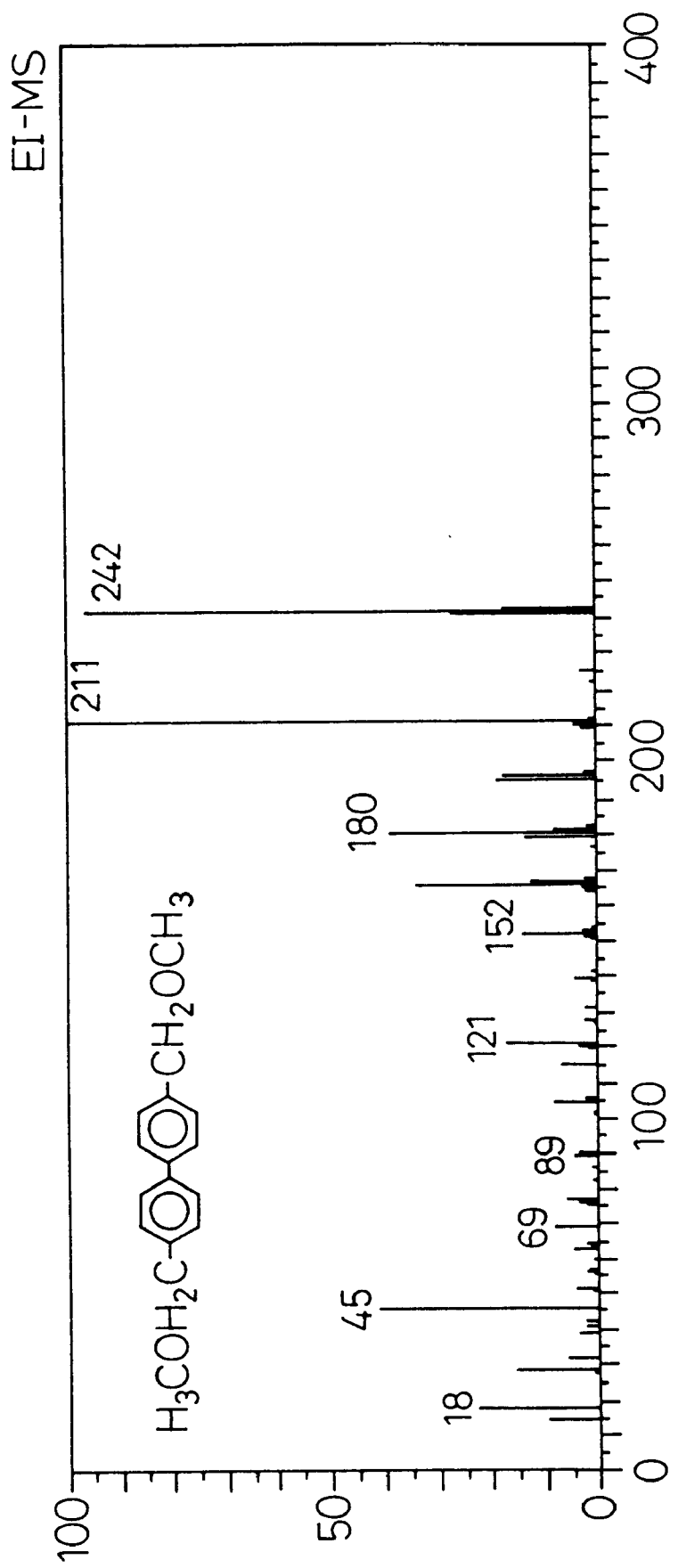
FIG. 4 is a mass analysis chart in Example 1-7.

The mass analysis (EI) was as shown in FIG. 4.

Figure 5:
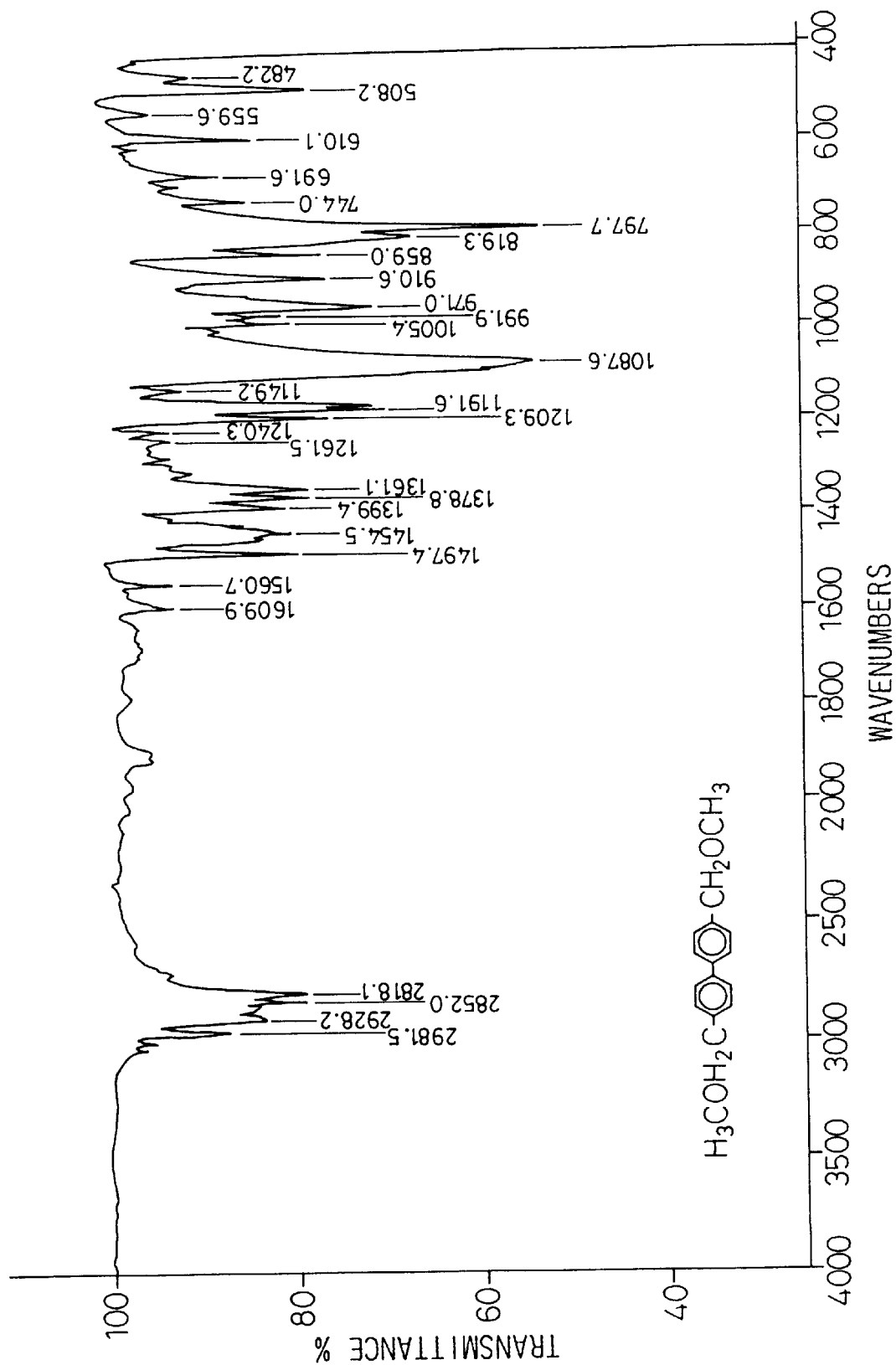
FIG. 5 is an infrared absorption spectrum in Example 1-7.

The infrared absorption spectrum was as shown in FIG. 5.

Figure 6:
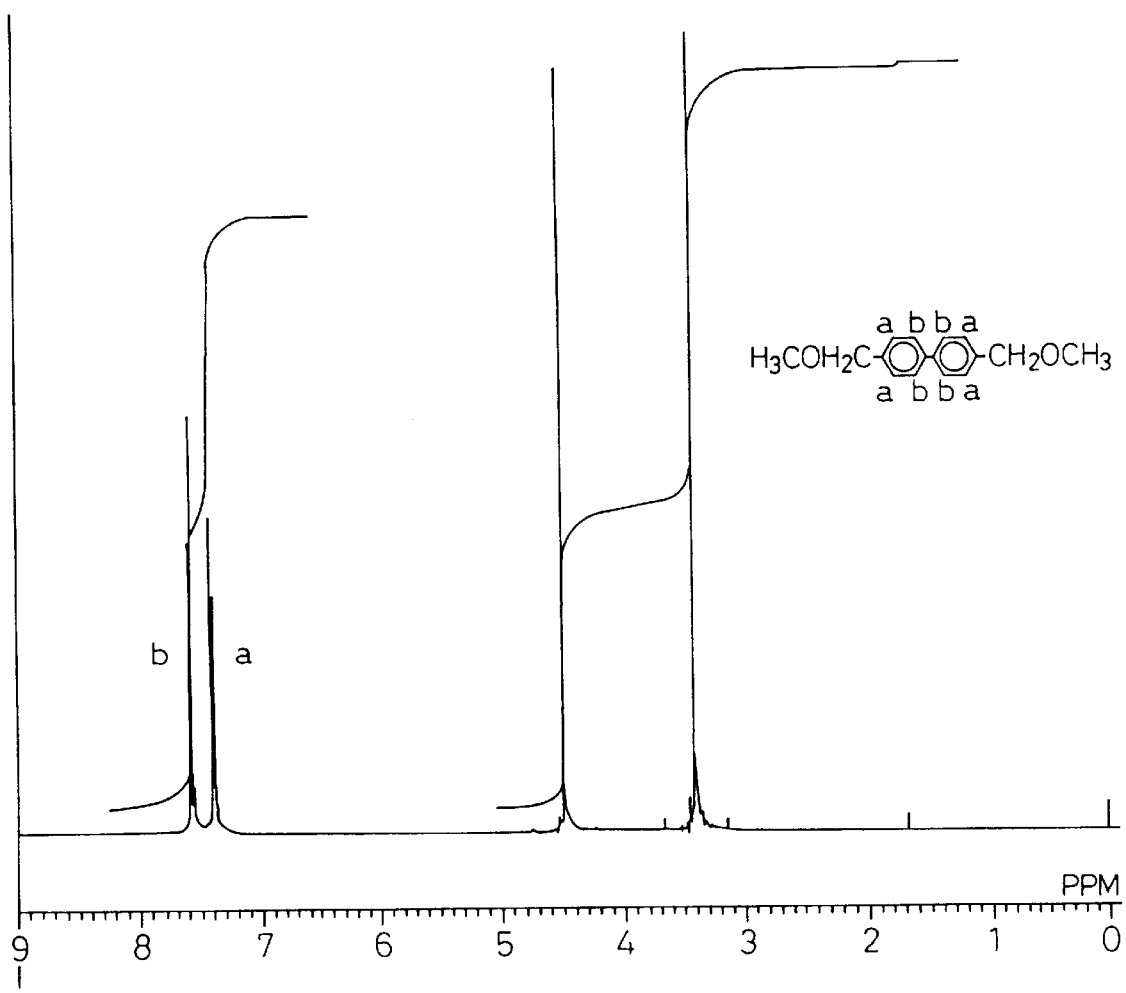
FIG. 6 is a result of ¹H-NMR obtained in Example 1-7.

The results of the $^1$H-NMR (solvent: CDCl$_3$) were as shown in FIG. 6.

Example 1-8

Synthesis of 2,4'-bis(methoxymethyl)biphenyl

When a mixture of the bis(methoxymethyl)biphenyl isomers obtained in Example 1-5 was cooled to 0° C., the 4,4'-isomer precipitates, so by quick filtering, a filtrate containing about 75% 2,4'-isomer was obtained.

This filtrate was distilled under reduced pressure at 180° C. and 3.5 Torr and the fraction at 155° C. was taken to obtain the 2,4'-bis(methoxymethyl)biphenyl. The purity was 92%.

Figure 7:
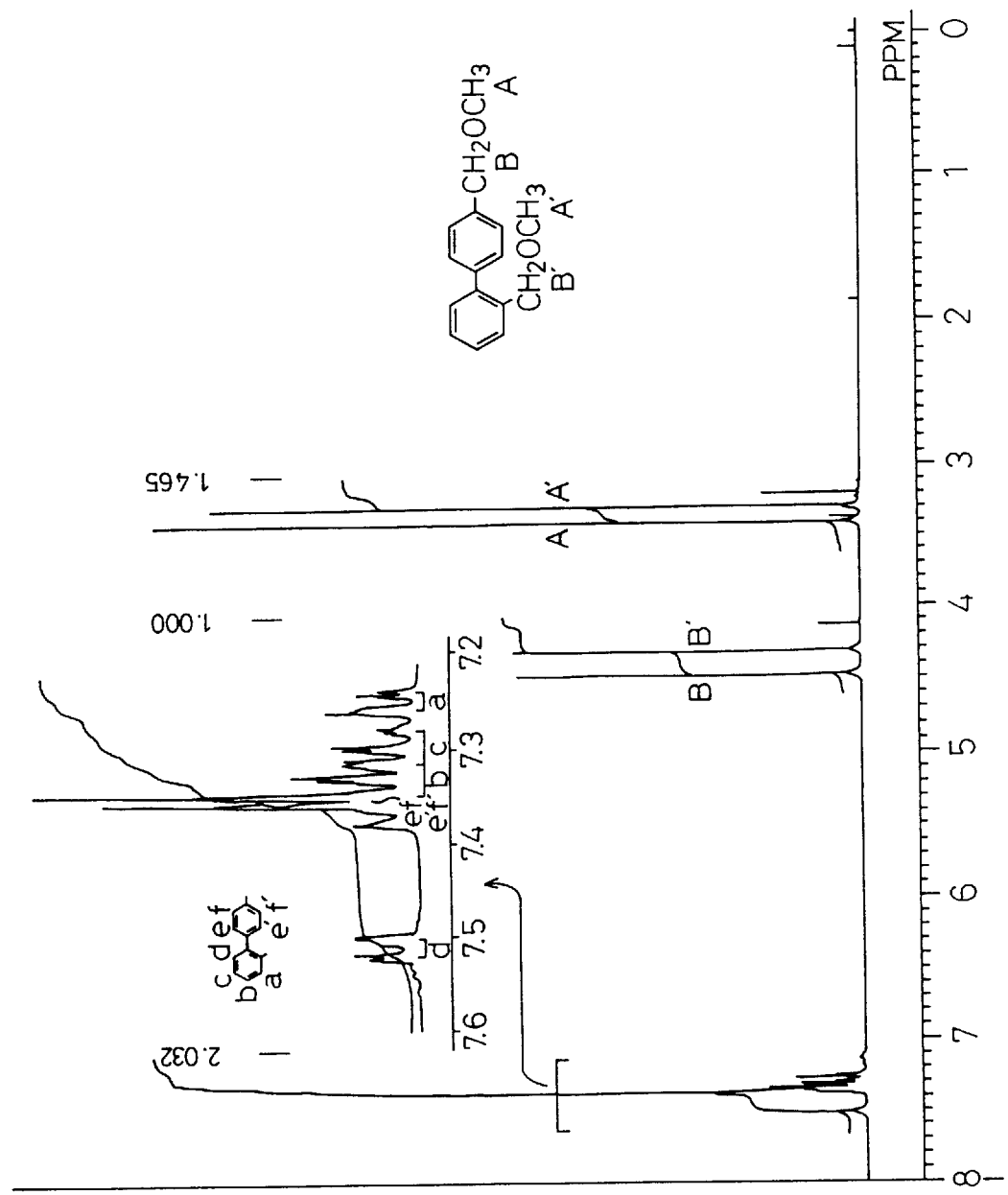
FIG. 7 is a mass analysis chart in Example 1-8.

The results of the $^1$H-NMR (solvent: CDCl$_3$) were as shown in FIG. 7. It was learned that there were eight types of the H of the benzene ring.

Figure 8:
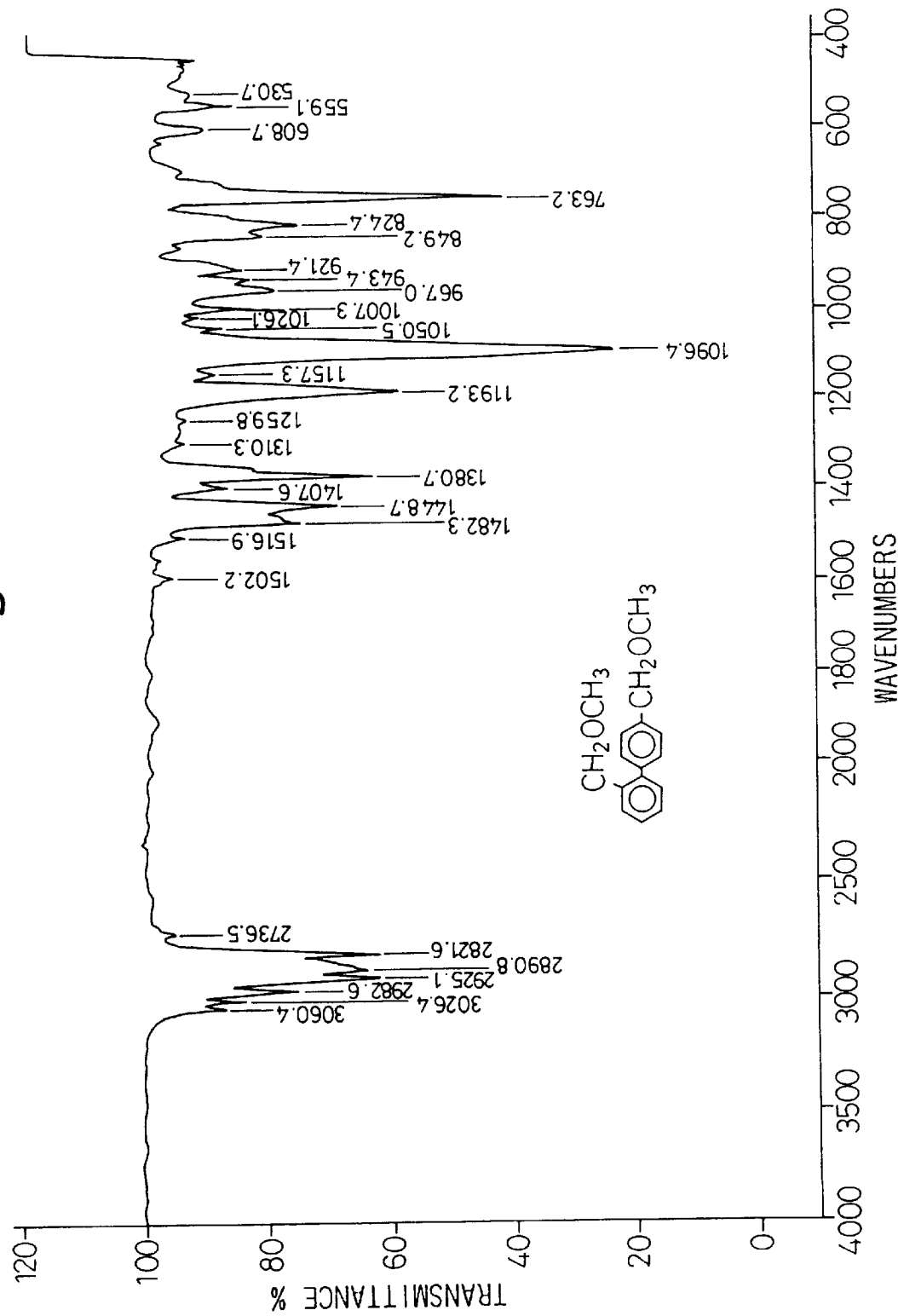
FIG. 8 is a result of ¹H-NMR obtained in Example 1-8.

The infrared absorption spectrum was as shown in FIG. 8.

The bis(methoxymethyl)biphenyl of the present invention can be used for the applications explained below.

The bis(methoxymethyl)biphenyl or the bis(methoxymethyl)biphenyl mixtures of the present invention may be allowed to react with phenol compounds to produce phenol novolak condensates.

These phenol novolak condensates may be used as epoxy resin curing agents or these phenol novolak condensates may be epoxidized to form epoxidized novolak resins.

Example 2-1

Synthesis of Phenol Novolak Condensate (Resin A)

564 g (6 moles) of phenol and 484 g (2 mole) of the mixture of general formula (I') (Ia:Ib:Ic:Id:Ie:If= 1:0.2:6:0.01:0.5:8.5) were charged into a flask provided with a stirrer and a cooler, then 15.4 g (0.1 mole) of diethyl sulfate was added dropwise. The reaction was continued for 3 hours while holding the reaction temperature at 160° C. During this time, the alcohol produced was removed by distillation.

Figure 9:
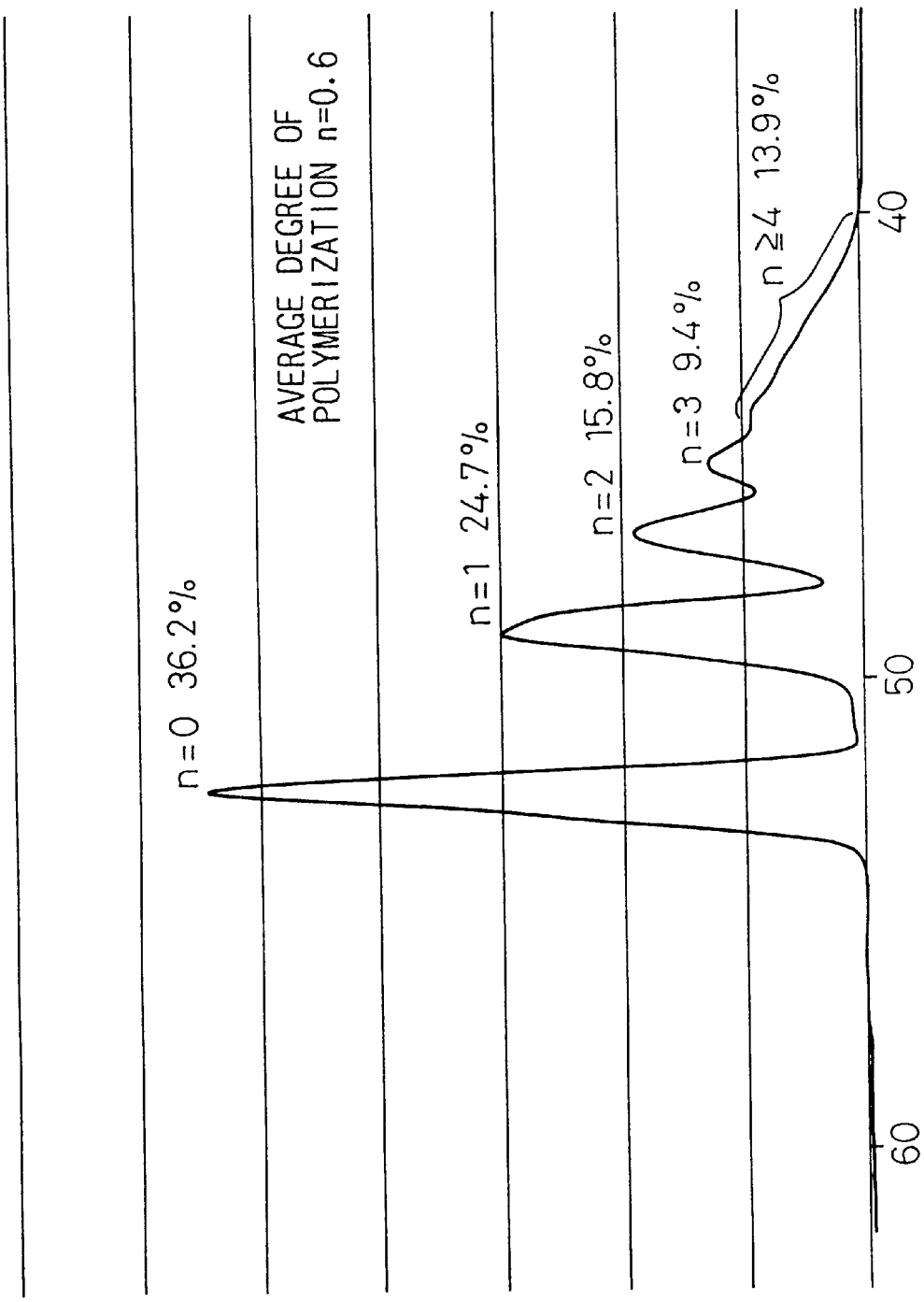
FIG. 9 is a GPC (i.e., gas permeation chromatography) chart of the resin obtained in Example 2-1.

After the reaction ended, the mixture was cooled, then washed with water three times. The oil layer was separated and the unreacted phenol was removed by distillation under reduced pressure to obtain 700 g of the resin (A). The softening point of the obtained resin (A) was 74° C. and the hydroxyl equivalent was 175 g/eq. The GPC (i.e., gel permeation chromatography) data of the resultant resin was shown in FIG. 9, which showed that the weight ratio of the condensates having n of 1 or more was 63.8% and the weight average of n was 0.6.

Example 2-2

Synthesis of Phenol Novolak Condensate (Resin B)

The same reaction was performed as in Example 2-1 except that 470 g of phenol was used to obtain 720 g of the resin (B). The softening point of the resin was 78° C. and the hydroxyl equivalent was 175 g/eq.

Figure 10:
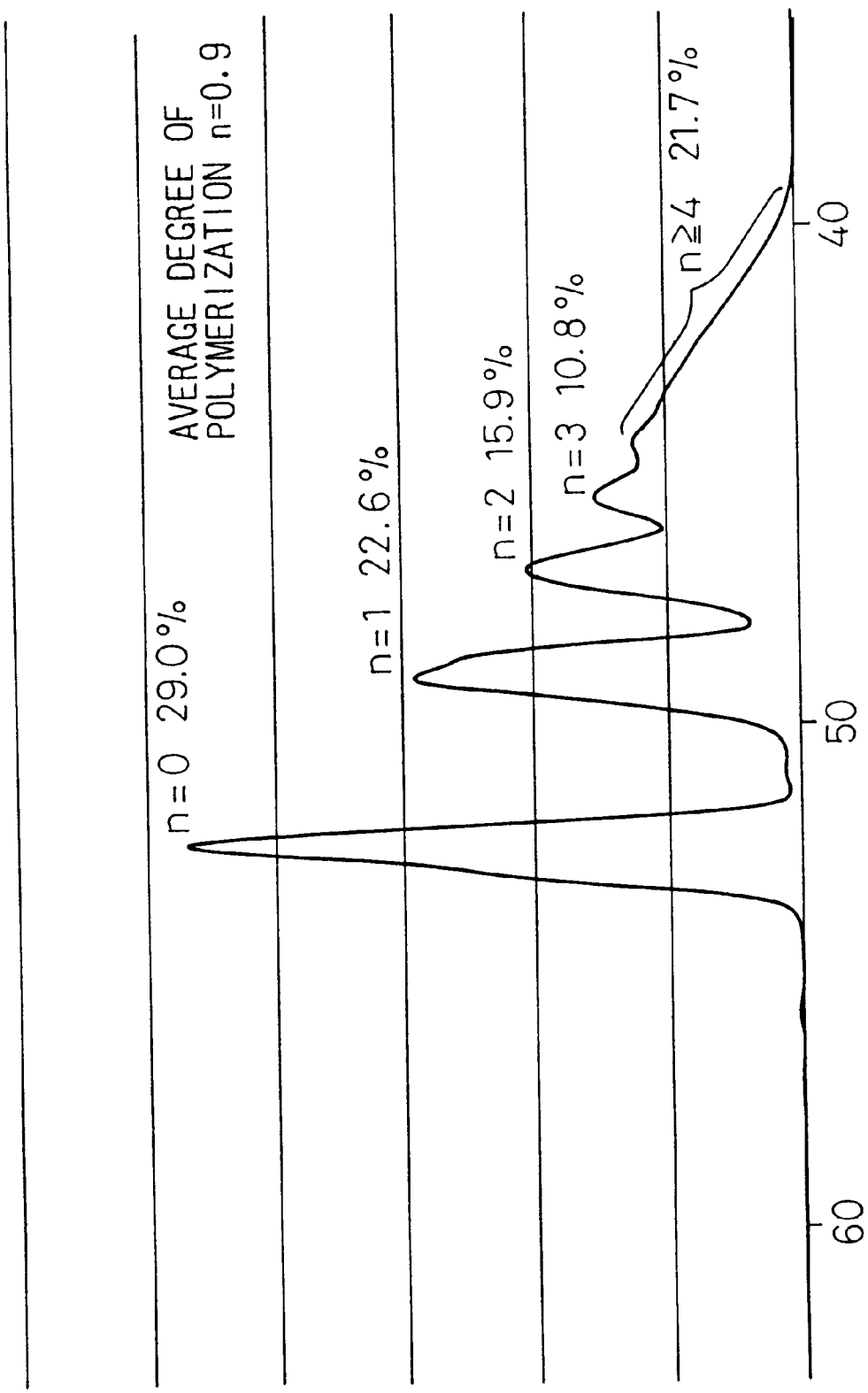
FIG. 10 is a GPC chart of the resin obtained in Example 2-2.

The GPC data of the resultant resin was shown in FIG. 10, which showed that the weight ratio of the condensates having n of 1 or more was 71.0% and the weight average of n was 0.9.

Example 2-3

Synthesis of Epoxidated Novolak Resin (Resin C)

175 g of the resin (A) obtained in Example 2-1, 555 g (6 mole) of epichlorohydrin, and 50 g of methanol were mixed and dissolved together. While holding the reaction temperature at 50° C., 40 g (1 mole) of solid NaOH was added bit by bit. After the end of the addition, the reaction was continued for 2 hours. The temperature was raised to 70° C., then the reaction was continued for two further hours.

After the end of the reaction, the byproduct salt was removed by washing with water, then the unreacted epichlorohydrin was removed by distillation under reduced pressure. 400 g of methylisobutylketone was added to the residue to make a uniform solution, then 20 g of a 20% aqueous solution of NaOH was added to the mixture, the temperature was raised to 70° C., and a reaction was caused for 1 hour.

After the end of the reaction, the mixture was washed with water a total of 5 times until the washings became neutral. The organic layer was separated and the methylisobutylketone was distilled off so as to obtain 228 g of the epoxy resin (C). The softening point of this resin was 60° C. and the epoxy equivalent was 239 g/eq.

Example 2-4

Synthesis of Epoxidated Novolak Resin (Resin D)

The same reaction was performed as in Example 2-3 except that 175 g of the resin (B) was used to obtain 225 g of the epoxy resin (D). The softening point of the resin was 64° C. and the epoxy equivalent was 239 g/eq.

Example 2-5

Synthesis of Phenol Novolak Condensate (Resin E)

The same procedure was performed as in Example 2-1 using 117.5 g (1.25 mole) of phenol and 121.0 g (0.50 mole) of 4,4'-bis(methoxymethyl)biphenyl and adding dropwise 0.11 ml of 48% sulfuric acid instead of diethyl sulfate. The reaction was caused for 3 hours holding the reaction temperature at 150° C. to obtain 158 g of the resin (E).

The softening point of the resultant resin (E) was 82.6° C. and the hydroxyl equivalent was 199 g/eq.

Figure 11:
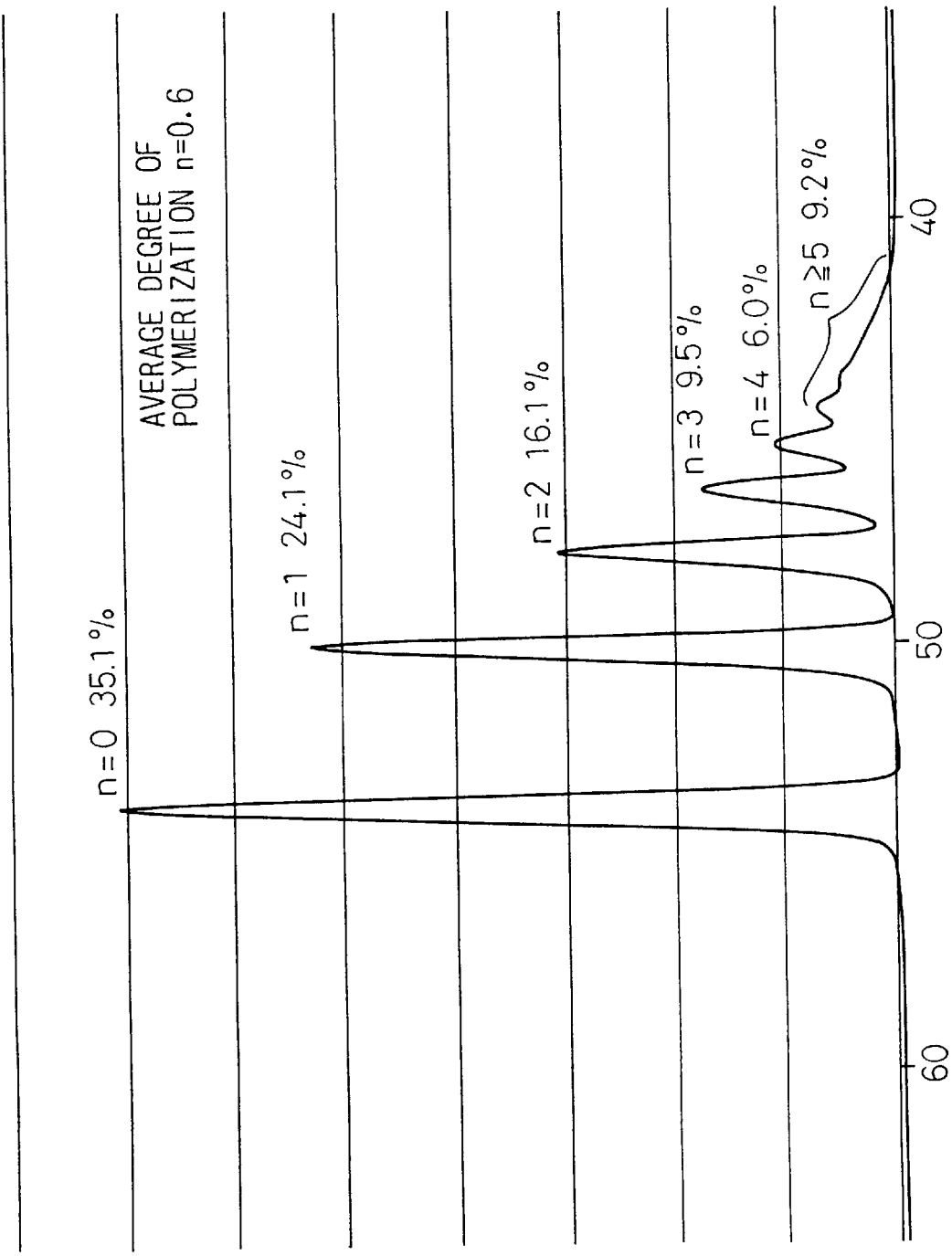
FIG. 11 is a GPC chart of the resin obtained in Example 2-5.

The GPC data of the resultant resin was shown in FIG. 11, which showed that the weight ratio of the condensates having n of 1 or more was 64.9%.

Example 2-6

Synthesis of Phenol Novolak Polycondensate (Resin F)

The same reaction was performed as in Example 2-5 except that a mixture of bis(methoxymethyl)biphenyl of 50% 2,4'-isomers and 50% 4,4'-isomers was used to obtain 156 g of the resin F.

The softening point of the resultant resin (F) was 82.0° C. and the hydroxyl equivalent was 199 g/eq.

The GPC data of the resultant resin was shown in FIG. 12, which showed that the weight ratio of the condensate having n of 1 or more was 68.5% and the weight average of n was 0.8.

The proportions of the formulations of the epoxy resin composition when using the resins (A), (B), (E), and (F) obtained in the above Examples as curing agents for epoxy resins, the properties of those cured products, the proportions of formulations of the epoxy resin compositions comprised of the resins (C) and (D) the epoxy curing agents, the properties of these cured products and, also, the proportions of the formulations of the epoxy resin composition comprised of the resin (C) as an epoxy resin and the resin (A) as a curing agent are shown in Table 1 and Table 2.

The phenol novolak resin in Tables 1 and 2 was the H-1 made by Meiwa Kasei K.K. (softening point 86° C., hydroxyl equivalent 104 g/eq), while the epoxidized-o-cresol novolak resin was the EOCN-1020 made by Nihon Kayaku K.K. (softening point 70° C., epoxy equivalent 200 g/eq). Silica used as a filler was RD-8 made by Tatumori Kagaku K.K. and triphenylphosphine was used as a curing accelerator.

Preparation of Test Pieces and Test Methods for Measurement of Physical Properties Shown in Table 1

The components shown in Table 1 were blended, then were heated to 150° C. to melt and mix. The mixture was deaerated by vacuum, then poured into a mold (thickness 4 mm) of 150° C. and allowed to cure (cured at 150° C. for 3 hours, then cured at 180° C. for 5 hours).

Test Methods

Water absorption rate: Dimensions of test pieces 25×70×4 mm, 24 hours, boiling method Breakage energy, flexural modulus, flexural strength: 3-point bending method, dimensions of test piece 4×6×70 mm Tg: TMA (Thermal Mechanical Analysis) method Preparation of Test Pieces and Test Method for Measurement of Physical Property Shown in Table 2

The adhesive of Table 2 was blended and melted at 150° C., then the melted adhesive was coated on 10 mm of one end of prestripped coating pieces (aluminum foil of 0.1× 20×100 mm). The coating pieces were stacked to adjust to a thickness of the adhesive of 0.1 mm, then were clamped in place and cured (cured at 150° C. for 3 hours, then cured at 180° C. for 5 hours). After curing, the T-type peel strength (bonding strength) was measured.

From the results of Table 1 and Table 2, it is understood that the phenol novolak condensate and epoxidized phenol resin using the compound of the formula (I) exhibited superior values in all properties, such as water absorption, mechanical properties, and bonding property compared with conventional products.

Further, the generation of flashes was not observed.

Examples of the formulations of the phenol resin compositions using the resin (A) and (B) obtained in Examples 2-1 and 2-2 and the properties of the cured products of the composition are shown in Table 3. The test specimens for the determination of various physical properties shown in Table 3 were prepared and the tests were carried out as follows.

The components shown in the formulation of Table 3 were mixed. After mixing, the mixture was placed in a mold for flexural strength test (size 10×10×100 mm) and molded and cured under a molding pressure of 200 kg/cm$^2$ at 160° C. for 5 minutes. After curing, the test specimens were heated at 250° C., 260° C. or 270° C. for 500 hours as a test for heat resistance thereof and, after cooling, the flexural strength was determined at an ordinary temperature.

As is clear from the results shown in Table 3, the phenol novolak resins obtained from the use of the compound (I') exhibit excellent values in the heat resistance and mechanical characteristics, compared with the conventional product.

TABLE 1

| Composition | Ex. 1 | Ex. 2 | Ex. 3 | Ex. 4 | Comp. Ex. 1 | Ex. 5 | Ex. 6 | Ex. 7 |
|---|---|---|---|---|---|---|---|---|
| Composition | | | | | | | | |
| Resin (A) (parts) | 91.5 | — | — | — | — | — | — | 73 |
| Resin (B) (parts) | — | 91.5 | — | — | — | — | — | — |
| Resin (C) (parts) | — | — | 100 | — | — | — | — | 100 |
| Resin (D) (parts) | — | — | — | 100 | — | — | — | — |
| Resin (E) (parts) | — | — | — | — | — | 99 | — | — |
| Resin (F) (parts) | — | — | — | — | — | — | 99 | — |
| Phenol novolak resin (parts) | — | — | 44 | 44 | 52 | — | — | — |
| Epoxidated o-cresol novolak resin (parts) | 100 | 100 | — | — | 100 | 100 | 100 | — |
| Triphenylphosphine (parts) | 0.24 | 0.24 | 0.24 | 0.24 | 0.24 | 0.275 | 0.31 | 0.24 |
| | Cured 1 | Cured 2 | Cured 3 | Cured 4 | Comp. Ex. | Cured 5 | Cured 6 | Cured 7 |
| Physical properties | | | | | | | | |
| Water absorption (%) | 0.83 | 0.78 | 0.71 | 0.72 | 1.10 | 0.81 | 0.80 | 0.65 |
| Breakage energy (kgf/mm) | 75.16 | 74.82 | 79.32 | 80.57 | 56.31 | 74.30 | 78.51 | 82.56 |
| Flexural modulus (kgf/mm$^2$) | 359.23 | 362.23 | 358.91 | 360.22 | 335.51 | 365.8 | 378.2 | 361.50 |
| Flexural strength (kgf/mm$^2$) | 15.46 | 16.31 | 16.42 | 16.22 | 14.96 | 15.20 | 16.60 | 17.02 |
| Tg (° C.) | 137 | 139 | 140 | 138 | 134 | 140 | 138 | 139 |

TABLE 2

| Composition | Ex. 1 | Ex. 2 | Ex. 3 | Ex. 4 | Comp. Ex. 1 | Ex. 5 | Ex. 6 | Ex. 7 |
|---|---|---|---|---|---|---|---|---|
| Composition | | | | | | | | |
| Resin (A) (parts) | 91.5 | — | — | — | — | — | — | 73 |
| Resin (B) (parts) | — | 91.5 | — | — | — | — | — | — |
| Resin (C) (parts) | — | — | 100 | — | — | — | — | 100 |
| Resin (D) (parts) | — | — | — | 100 | — | — | — | — |
| Resin (E) (parts) | — | — | — | — | — | 99 | — | — |
| Resin (F) (parts) | — | — | — | — | — | — | 99 | — |
| Phenol novolak resin (parts) | — | — | 44 | 44 | 52 | — | — | — |
| Epoxidated o-cresol novolak resin (parts) | 100 | 100 | — | — | 100 | 100 | 100 | — |
| Triphenylphosphine (parts) | 0.24 | 0.24 | 0.24 | 0.24 | 0.24 | 0.275 | 0.31 | 0.24 |
| Silica (parts) | 191.74 | 191.74 | 144.24 | 144.24 | 152.24 | 199.28 | 199.31 | 173.24 |
| | Cured 1 | Cured 2 | Cured 3 | Cured 4 | Comp. Ex. | Cured 5 | Cured 6 | Cured 7 |
| Bonding strength (g/cm) | 960 | 813 | 1015 | 1020 | 50 | 960 | 950 | 1110 |

TABLE 3

| | Composition 8 | Composition 9 | Comparative Example |
|---|---|---|---|
| Formulation (wt. parts) | | | |
| Resin (A) | 100 | — | — |
| Resin (B) | — | 100 | — |
| Phenol Novolak Resin[*1] | — | — | 100 |
| Hexamethylenetetramine | 17 | 17 | 17 |
| Glass fiber[*2] | 70 | 70 | 70 |
| Physical Properties | | | |
| Flexural strength (kgf/mm$^2$) (250° C. × 500 hr) | 20.6 | 21.3 | 5.8 |
| " (260° C. × 500 hr) | 19.6 | 19.8 | 4.7 |
| " (270° C. × 500 hr) | 19.1 | 18.7 | 3.5 |

[*1]Conventional resin (phenol novolak resin H-1, s.p. = 86° C., available from Meiwa Kasei K.K.)
[*2]Chopped strand (5 mm) available from Nittobo K.K.

According to the present invention, it is possible to industrially and economically produce various types of bis(methoxymethyl)biphenyl isomers and mixtures thereof using a nickel complex-metal powder catalyst system and through a dehalogenating coupling reaction of a halogenated methoxymethylbenzene. It is possible to economically provide a novel bis(methoxymethyl)biphenyl which is a useful intermediate, but for which there has been no effective means of synthesis.

Further, the present invention provides a novel phenol novolak condensate which can be used for a thermosetting resin, a curing agent of an epoxy resin, the starting material of an epoxidized novolak resin, etc. The phenol novolak condensate and epoxidized phenol resin of the present invention are superior to conventional products in the water absorption property, mechanical properties, bonding properties, etc. Furthermore, bis(methoxymethyl)biphenyl is produced in the reaction at the time of production. There is no particular need for refinement. The reaction is a demethanolation reaction as opposed to the prior art, which was a dehydration reaction, and therefore is also advantageous technically and economically.

We claim:

1. An epoxy resin composition comprising a phenol novolak condensate obtained from a reaction between (a) a mixture of isomers of a bis(methoxymethyl)biphenyl having the formula (I') including at least 40% by weight of a mixture of a 2,4'-isomer of bis(methoxymethyl)biphenyl and a 4,4'-isomer of bis(methoxymethyl)biphenyl, wherein the mixture of isomers includes at least 5% by weight of a 2,4'-isomer of bis(methoxymethyl)biphenyl, and (b) a phenol compound, wherein formula (I') is as follows:

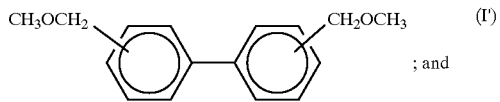
; and an epoxy resin.

2. An epoxy resin composition according to claim 1, wherein the mixture of isomers includes at least 40% by weight of a 2,4'-isomer of bis(methoxymethyl)biphenyl.

3. An epoxy resin composition according to claim 1, wherein the mixture of isomers includes at least 10% by weight of a 2,4'-isomer of bis(methoxymethyl)biphenyl.

4. An epoxidized novolak resin obtained by epoxidizing a phenol novolak condensate obtained from a reaction between (a) a mixture of isomers of a bis(methoxymethyl)biphenyl having the formula (I') including at least 40% by weight of a mixture of a 2,4'-isomer of bis(methoxymethyl)biphenyl and a 4,4'-isomer of bis(methoxymethyl)biphenyl, wherein the mixture of isomers includes at least 5% by weight of a 2,4'-isomer of bis(methoxymethyl)biphenyl, and (b) a phenol compound, wherein formula (I') is as follows:

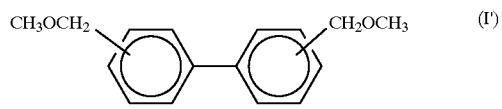

5. An epoxy resin composition comprising an epoxidized novolak resin obtained by epoxidizing a phenol novolak condensate obtained from a reaction between (a) a mixture of isomers of a bis(methoxymethyl)biphenyl having the formula (I') including at least 40% by weight of a mixture of a 2,4'-isomer of bis(methoxymethyl)biphenyl and a 4,4'-isomer of bis(methoxymethyl)biphenyl, wherein the mixture of isomers includes at least 5% by weight of a 2,4'-isomer of bis(methoxymethyl)biphenyl, and (b) a phenol compound, wherein formula (I') is as follows:

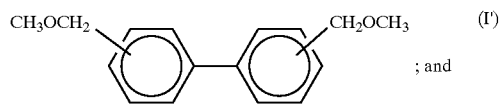
; and a curing agent for an epoxy resin.

6. An epoxy resin composition comprising an epoxidized novolak resin obtained by epoxidizing a phenol novolak condensate obtained from a reaction between (a) a mixture of isomers of a bis(methoxymethyl)biphenyl having the formula (I') including at least 40% by weight of a mixture of a 2,4'-isomer of bis(methoxymethyl)biphenyl and a 4,4'-isomer of bis(methoxymethyl)biphenyl, wherein the mixture of isomers includes at least 5% by weight of a 2,4'-isomer of bis(methoxymethyl)biphenyl, and (b) a phenol compound, wherein formula (I') is as follows:

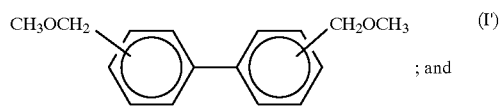
; and the phenol novolak condensate obtained from a reaction between (a) a mixture of isomers of a bis(methoxymethyl) biphenyl having the formula (I') and (b) a phenol compound, as a curing agent for an epoxy resin.

7. An epoxy resin composition according to any one of claims 1 and 4–6, wherein the phenol compound includes a member selected from the group consisting of: phenol, resorcinol, hydroquinone, cresol, ethylphenol, n-propylphenol, iso-propylphenol, t-butylphenol, octylphenol, nonylphenol, phenylphenol, xylenol, methylpropylphenol, methylbutylphenol, methylhexylphenol, dipropylphenol, dibutylphenol, guaiacol, catechol ethyl ether, trimethylphenol, naphthol, methylnaphthol, bisphenol A, and bisphenol F.

* * * * *